US008367331B2

(12) United States Patent
Feehery et al.

(10) Patent No.: US 8,367,331 B2
(45) Date of Patent: Feb. 5, 2013

(54) METHOD FOR ENRICHING METHYLATED CPG SEQUENCES

(75) Inventors: George R. Feehery, West Newbury, MA (US); Sriharsa Pradhan, Wenham, MA (US)

(73) Assignee: New England Biolabs, Inc., Ipswich, MA (US)

(*) Notice: Subject to any disclaimer, the term of this patent is extended or adjusted under 35 U.S.C. 154(b) by 364 days.

(21) Appl. No.: 12/608,489

(22) Filed: Oct. 29, 2009

(65) Prior Publication Data
US 2010/0112585 A1 May 6, 2010

Related U.S. Application Data

(60) Provisional application No. 61/111,499, filed on Nov. 5, 2008.

(51) Int. Cl.
*C12Q 1/68* (2006.01)
(52) U.S. Cl. ............................................. 435/6.1
(58) Field of Classification Search ............... 435/6.1
See application file for complete search history.

(56) References Cited

PUBLICATIONS

Accession No. EF560733 (2007)—reference embedded in the Office Action.*
Bird, A P (1986) Cpg-rich islands and the function of DNA methylation. Nature 321: 209-213.
Bird, A P (2002) DNA methylation patterns and epigenetic memory. Genes Dev 16: 6-21.
Borczuk A C, Kim H K, Yegen H A, et al. (2005) Lung Adenocarcinoma Global Profiling Identifies Type II Transforming Growth Factor-ss Receptor as a Repressor of Invasiveness. American Journal of Respiratory and Critical Care Medicine, 172: 729-737.
Bostick M, Kim J K, Esteve P O, Clark A, Pradhan S, Jacobsen S (2007) UHRF1 Plays a Role in Maintaining DNA Methylation in Mammalian Cells Science 21(317): 1760-1764.
Boumber Y A, Kondo Y, Chen X, Shen L, Gharibyan V, et al.,Kazuo, (2007) RIL, a LIM Gene on 5q31, Is Silenced by Methylation in Cancer and Sensitizes Cancer Cells to Apoptosis. Cancer Research 67: 1997-2005.
Collins et al., PNAS USA, 84, 4393-4397, 1987.
Carrasco D, Tonon G , Huang Y, Zhang Y, Sinha R, Feng B, Stewart J, Zhan F, Khatry D, Protopopova, M. (2003) High-resolution genomic profiles define distinct clinicopathogenetic subgroups of multiple myeloma patients. Cancer Cell, 9(4): 313-325.
Cokus S, Feng S, Zhang X, Chen Z, Merriman B, Haudenschild C, Pradhan S, Nelson S, Pellegrini M, Jacobsen S (2008) Shotgun bisulphite sequencing of the Arabidopsis genome reveals DNA methylation patterning. Nature 452, 215-219.
Das R, Dimitrova N, Xuan Z, Rollins R, et al. (2006) Computational prediction of methylation status in human genomic sequences. PNAS 103 (28): 10713-10716.
Deininger PL, Batzer MA. (2002) Mammalian retroelements. Genome Research. 12(10): 1455-1465.
Filion G J P, Zhenilo S. Salozhin S, Yamada D, Prokhortchouk E, Pierre-Defossez P A. (2006) A Family of Human Zinc Finger Proteins That Bind Methylated DNA and Repress Transcription Mol Cell Biol. 26(1): 169-181.
Frommer M, McDonald LE, Millar DS, Collis CM, Watt F, Grigg GW, Molloy PL, Paul CL (1992) A genomic sequencing protocol that yields a positive display of 5-methylcytosine residues in individual DNA strands. Proc Natl Acad Sci U S A 89:1827-183.
Heard E, Clerc P, Avner P (1997) X-Chromosome inactivation in mammals. Annu Rev Gent 31: 571-610.
Hendrich B, Bird A (1998) Identification and Characterization of a Family of Mammalian Methyl-CpG Binding Proteins. Mol Cell Biol. 18(11): 6538-6547.
Herman JG, Graff JR, Myohanen S, Nelkin BD, Baylin SB: Methylation-specific PCR: a novel PCR assay for methylation status of CpG islands. Proc Natl Acad Sci U S A 1996, 93:9821-9826.
Illingworth R, Kerr A, DeSousa D, Jorgensen H, Ellis P, et al. (2008) A novel CpG island set identifies tissue-specific methylation at developmental gene loci. PloS Biol 6(1): e22.
Jacquemont C, Taniguchi T, The Fanconi anemia pathway and ubiquitin (2007) BMC Biochem., 8(Suppl 1): S10.
Li Z X, Ma X, Wang Z H. (2006) A differentially methylated region of the DAZ1 gene in spermatic and somatic cells. Asian Journal of Andrology. 8(1): 61-67.
Lu S, Davies P, Regulation of the expression of the tissue transglutaminase gene byoDNAomethylation. (1997) PNAS, 94(9): 4692-4697.
Reik W (2007) Stability and flexibility of epigenetic gene regulation in mammalian development. Nature 447: 425-432.
Reinders J, Celine Delucinge Vivier C D, Theiler G, Chollet D, Descombes P, Paszkowski J (2008) Genome-wide, high-resolution DNA methylation profiling using bisulfate mediated cytosine conversion. Genome Res. 18(3): 469-476.
Rousseaux S, Caron C, Govin J, Lestrat C, Faure A K, Khochbin S, (2005) Establishment of male-specific epigenetic information. Gene, 345 (2): 139-153.
Sado T, Fenner MH, Tan SS,Tam P, Shioda T, et al. (2000) X inactivation in the mouse embryo deficient for Dnmt1: distinct effect of hypomethylation on imprinted and random X inactivation. Dev Biol 225: 294-303.
Shen L, Kondo Y,Guo Y, Zhang J, Zhang L, et al. (2007) Genome-wide profiling of DNA methylation reveals a class of normally methylated CpG island promoters. PloS Genet (10): e181.
Song L, James S R, Kazim L, Karpf A (2005) Specific Method for the Determination of Genomic DNA Methylation by Liquid Chromatography-Electrospray Ionization Tandem Mass Spectrometry. Anal. Chem., 775 (2): 504-510.
Ueki T, Walter K, Skinner H, Jaffee E, et al. (2002) Aberrant CpG island methylation in cancer cell lines arises in the primary cancers from which they were derived. Oncogene 21(13): 2114-2117.
Xiong Z, Laird P, (1997) COBRA: a sensitive and quantitative DNA methylation assay. Nucleic Acids Research 25(12): 2532-2534.
Shiraishi et al, Proc. Natl. Acad. Sci. USA, 96, 2913-2918, 1999.
Shiraishi et al, Analytical Biochemistry, 329, 1-10, 2004.

* cited by examiner

*Primary Examiner* — Tekchand Saidha
(74) *Attorney, Agent, or Firm* — New England Biolabs, Inc; Harriet M. Strimpel

(57) ABSTRACT

Compositions and methods are provided for facilitating the enrichment of single-stranded DNA containing methylated CpG in a mixture containing methylated and unmethylated DNA. The compositions relate to methylation-binding protein domains that selectively bind to methylated single strand DNA. In embodiments of the invention, the methylated DNA is eluted in 0.4M-0.6M NaCl while the unmethylated single strand DNA is eluted in less than 0.4M salt. The ability to readily enrich for methylated DNA permits high throughput sequencing of the methylated DNA and identification of abnormal methylation patterns associated with disease.

4 Claims, 10 Drawing Sheets

Figure 7     DNA alignment mouse/human SRA domains

```
Mouse  CCCG-CCAACCACTTCGGGCCCATCCCTGGTGTCCCTGTGGGCACCATGTGGCGCTTCAG
       ||||  ||||||||| ||||||||||||||||||||||||| |||||||||||||  | 
Human  CCCGTCCAACCACTACGGACCCATCCCGGGGATCCCCGTGGGCACCATGTGGCGGTTCCG Mouse  AGTCCAGGTCAGTGAGTCCGGTGTGCATCGGCCTCATGTGGCAGGCATCCATGGCCGGAG
       |||||||||||||| ||| ||||||| |||||||||||||||||||||||||||||||||
Human  AGTCCAGGTCAGCGAGTCGGGTGTCCATCGGCCCCACGTGGCTCATCGGCATCCATGGCCGGAG Mouse  CAACGACGGTGCCTACTCATTGGTCCTGCTGGTGCTATGAGGATGATGTGACAATGG
       |||||||||||||||||| |  ||||||||||||||||||||||||||||| ||||||
Human  CAACGACGGATCGTACTCCCTAGTCCTGCTGGCGGGGGGCTATGAGGATGATGTGGACCATGG Mouse  CAATTACTTCACATACACAGGGAGTGGTGGCCGAGACCTCTCTGGCAACAAGCGTACAGC
       ||||| ||||||||||||||| ||||||||| ||||||  | |||||||||||||||| 
Human  GAATTTTTCACATACACGGGGTAGTGGTGTCGGGGATCTTTCCGGCAACAAGAGGACCGC Mouse  AGGCCAGTCCTCTGACCAGAGAGCTCACTAATAACAATAGGGCTCTGGCACTCAATTGCCA
       |||||  ||||| |||||||||||||||| || |||||||| ||||||||||||||||
Human  GGAACAGTCTTGTGATCAGAAACTCACCACCACCACGGGCGTGCTGGCCTCTCCAACTGCTT Mouse  CTCCCAATCAATG--AGAAAGGTGCGGAGGCTGAAGACTGGCGCCAAGGGAAGCCAGT
       |||||| ||||||  ||||||||||||||||||||||||| ||||||||||||||||||
Human  TGCTCCCATCAATGACCAAGAAGGGGCCGAGGCCAAGGACTGGCGGTCGGGGAAGCCGGT Mouse  GCGTGTGGTCCGGAACATGAAGGGCGGGAAACACAGCAAGTACGCTCCTGCAGAGGGCAA
       |||||||||  ||||||||||| ||||||  |||||| ||||||||||  || ||||||||
Human  CAGGGTGGTGCGCGAATGTCAAGGGTGGCAAGAATGCAAGTACGCGCCCCGCTGAGGGCAA Mouse  CCGCTATGATGGCATCTACAAGGTGTGAAGTACTGCCAGAGAGAGGGAAATCTGGCTT
       ||||||| ||||||||||||||| ||||| |||| ||||||||||||||||||||||
Human  CCGCTACGATGGCATCTACAAGGTTGTGAAATACTGCCCGAGAAGGGGAAGTCCGGGTT Mouse  CCTCGTGTGGGCGTTATCTCCT (SEQ ID NO:4)
       |||||||||||||||| ||| ||
Human  TCTCGTGTGGGCGCTACCTTCT (SEQ ID NO:5)
```

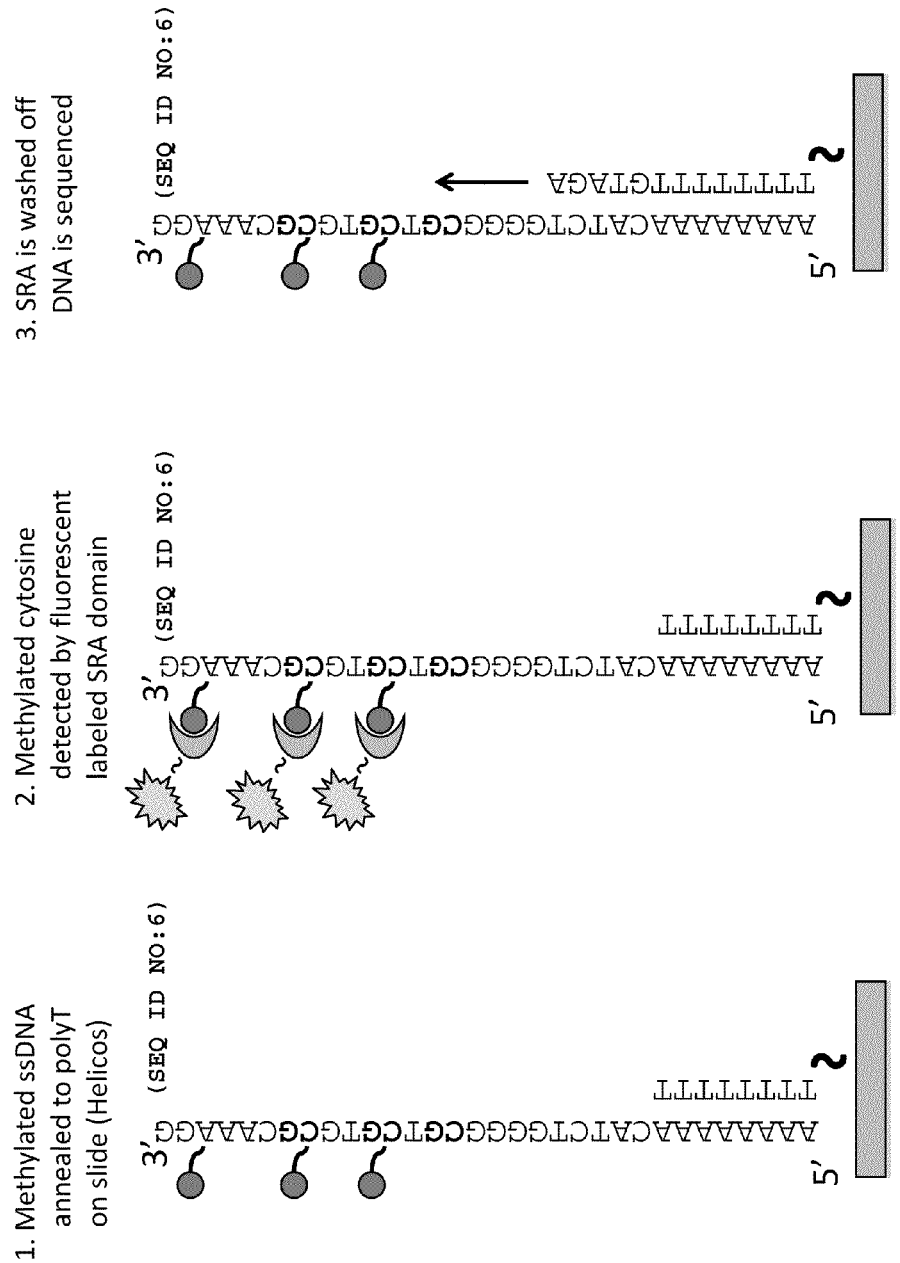

SEQUENCE LISTING

```
<160> NUMBER OF SEQ ID NOS: 79

<210> SEQ ID NO 1
<211> LENGTH: 22
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (19)..(22)
<223> OTHER INFORMATION: n= a, c, g or t

<400> SEQUENCE: 1
gtttcccagt caggatccnn nn                                              22

<210> SEQ ID NO 2
<211> LENGTH: 166
<212> TYPE: PRT
<213> ORGANISM: mouse

<400> SEQUENCE: 2

Pro Ala Asn His Phe Gly Pro Ile Pro Gly Val Pro Val Gly Thr Met
1               5                   10                  15

Trp Arg Phe Arg Val Gln Val Ser Glu Ser Gly Val His Arg Pro His
```

```
                           20                  25                  30
Val Ala Gly Ile His Gly Arg Ser Asn Asp Gly Ala Tyr Ser Leu Val
                35                  40                  45

Leu Ala Gly Gly Tyr Glu Asp Val Asp Asn Gly Asn Tyr Phe Thr
50                  55                  60

Tyr Thr Gly Ser Gly Gly Arg Asp Leu Ser Gly Asn Lys Arg Thr Ala
65                  70                  75                  80

Gly Gln Ser Ser Asp Gln Lys Leu Thr Asn Asn Arg Ala Leu Ala
                85                  90                  95

Leu Asn Cys His Ser Pro Ile Asn Glu Lys Gly Ala Glu Ala Glu Asp
                100                 105                 110

Trp Arg Gln Gly Lys Pro Val Arg Val Val Arg Asn Met Lys Gly Gly
                115                 120                 125

Lys His Ser Lys Tyr Ala Pro Ala Glu Gly Asn Arg Tyr Asp Gly Ile
                130                 135                 140

Tyr Lys Val Val Lys Tyr Trp Pro Glu Arg Gly Lys Ser Gly Phe Leu
145                 150                 155                 160

Val Trp Arg Tyr Leu Leu
                165

<210> SEQ ID NO 3
<211> LENGTH: 167
<212> TYPE: PRT
<213> ORGANISM: Homo sapiens

<400> SEQUENCE: 3

Pro Ser Asn His Tyr Gly Pro Ile Pro Gly Ile Pro Val Gly Thr Met
1               5                   10                  15

Trp Arg Phe Arg Val Gln Val Ser Glu Ser Gly Val His Arg Pro His
                20                  25                  30

Val Ala Gly Ile His Gly Arg Ser Asn Asp Gly Ala Tyr Ser Leu Val
                35                  40                  45

Leu Ala Gly Gly Tyr Glu Asp Val Asp His Gly Asn Phe Phe Thr
50                  55                  60

Tyr Thr Gly Ser Gly Gly Arg Asp Leu Ser Gly Asn Lys Arg Thr Ala
65                  70                  75                  80

Glu Gln Ser Cys Asp Gln Lys Leu Thr Asn Thr Asn Arg Ala Leu Ala
                85                  90                  95

Leu Asn Cys Phe Ala Pro Ile Asn Asp Gln Glu Gly Ala Glu Ala Lys
                100                 105                 110

Asp Trp Arg Ser Gly Lys Pro Val Arg Val Val Arg Asn Val Lys Gly
                115                 120                 125

Gly Lys Asn Ser Lys Tyr Ala Pro Ala Glu Gly Asn Arg Tyr Asp Gly
                130                 135                 140

Ile Tyr Lys Val Val Lys Tyr Trp Pro Glu Lys Gly Lys Ser Gly Phe
145                 150                 155                 160

Leu Val Trp Arg Tyr Leu Leu
                165

<210> SEQ ID NO 4
<211> LENGTH: 497
<212> TYPE: DNA
<213> ORGANISM: mouse

<400> SEQUENCE: 4
cccgccaacc acttcgggcc catccctggt gtccctgtgg gcaccatgtg gcgcttcaga       60
```

```
gtccaggtca gtgagtccgg tgtgcatcgg cctcatgtgg caggcatcca tggccggagc    120
aacgacggtg cctactcatt ggtcctggct ggtggctatg aggatgatgt ggacaatggc    180
aattacttca catacacagg gagtggtggc cgagacctct ctggcaacaa gcgtacagca    240
ggccagtcct ctgaccagaa gctcactaat aacaataggg ctctggcact caattgccac    300
tccccaatca atgagaaagg tgcggaggct gaagactggc gccaagggaa gccagtgcgt    360
gtggtccgga acatgaaggg cgggaaacac agcaagtacg ctcctgcaga gggcaaccgc    420
tatgatggca tctacaaggt ggtgaagtac tggccagaga gagggaaatc tggcttcctc    480
gtgtggcgtt atctcct                                                  497

<210> SEQ ID NO 5
<211> LENGTH: 501
<212> TYPE: DNA
<213> ORGANISM: Homo sapiens

<400> SEQUENCE: 5
cccgtccaac cactacggac ccatcccggg gatcccgtg ggcaccatgt ggcggttccg     60
agtccaggtc agcgagtcgg gtgtccatcg gccccacgtg gctggcatcc atggccggag   120
caacgacgga tcgtactccc tagtcctggc gggggctat gaggatgatg tggaccatgg    180 gaatttttc acatacacgg gtagtggtgg tcgagatctt tccggcaaca agaggaccgc    240
ggaacagtct tgtgatcaga aactccaccaa caccaacagg gcgctggctc tcaactgctt   300
tgctcccatc aatgaccaag aaggggccga ggccaaggac tggcggtcgg ggaagccggt   360
cagggtggtg cgcaatgtca agggtggcaa gaatagcaag tacgcccccg ctgagggcaa   420
ccgctacgat ggcatctaca aggttgtgaa atactggccc gagaagggga agtccgggtt   480
tctcgtgtgg cgctaccttc t                                             501

<210> SEQ ID NO 6
<211> LENGTH: 32
<212> TYPE: DNA
<213> ORGANISM: artificial
<220> FEATURE:
<223> OTHER INFORMATION: example of methylated sequence

<400> SEQUENCE: 6
aaaaaaaaca tctggggcgt cgtgcgcaaa gg                                   32

<210> SEQ ID NO 7
<211> LENGTH: 29
<212> TYPE: DNA
<213> ORGANISM: artificial
<220> FEATURE:
<223> OTHER INFORMATION: methylated oligonucleotide
<220> FEATURE:
<221> NAME/KEY: misc_feature
<222> LOCATION: (6)..(6)
<223> OTHER INFORMATION: artificially methylated cytosine
<220> FEATURE:
<221> NAME/KEY: misc_feature
<222> LOCATION: (16)..(16)
<223> OTHER INFORMATION: artificially methylated cytosine

<400> SEQUENCE: 7
gtaggcggtg ctacacggtt cctgaagtg                                       29

<210> SEQ ID NO 8
<211> LENGTH: 56
<212> TYPE: DNA
<213> ORGANISM: artificial
<220> FEATURE:
```

-continued

```
<223> OTHER INFORMATION: unmethylated oligonucleotide

<400> SEQUENCE: 8
gtcactgaag cgggaaggga ctggctgctc ccgggcgaag tgccggggca ggatct       56

<210> SEQ ID NO 9
<211> LENGTH: 23
<212> TYPE: DNA
<213> ORGANISM: artificial
<220> FEATURE:
<223> OTHER INFORMATION: primer

<400> SEQUENCE: 9
tcctggcaag ataaggagtt gac                                            23

<210> SEQ ID NO 10
<211> LENGTH: 23
<212> TYPE: DNA
<213> ORGANISM: artificial
<220> FEATURE:
<223> OTHER INFORMATION: primer

<400> SEQUENCE: 10
acacacgata gccctagcag ttc                                            23

<210> SEQ ID NO 11
<211> LENGTH: 19
<212> TYPE: DNA
<213> ORGANISM: artificial
<220> FEATURE:
<223> OTHER INFORMATION: primer

<400> SEQUENCE: 11
ggctcaagct ggcattcct                                                 19

<210> SEQ ID NO 12
<211> LENGTH: 23
<212> TYPE: DNA
<213> ORGANISM: artificial
<220> FEATURE:
<223> OTHER INFORMATION: primer

<400> SEQUENCE: 12
ggcttaatca cgcactgagc tta                                            23

<210> SEQ ID NO 13
<211> LENGTH: 20
<212> TYPE: DNA
<213> ORGANISM: artificial
<220> FEATURE:
<223> OTHER INFORMATION: primer

<400> SEQUENCE: 13
caaggcaaag cgaaattggt                                                20

<210> SEQ ID NO 14
<211> LENGTH: 21
<212> TYPE: DNA
<213> ORGANISM: artificial
<220> FEATURE:
<223> OTHER INFORMATION: primer

<400> SEQUENCE: 14
gcccgttcag tctcttcgat t                                              21

<210> SEQ ID NO 15
```

```
<211> LENGTH: 17
<212> TYPE: DNA
<213> ORGANISM: artificial
<220> FEATURE:
<223> OTHER INFORMATION: primer

<400> SEQUENCE: 15
tcatctgggg cgtcgtg                                                    17

<210> SEQ ID NO 16
<211> LENGTH: 17
<212> TYPE: DNA
<213> ORGANISM: artificial
<220> FEATURE:
<223> OTHER INFORMATION: primer

<400> SEQUENCE: 16
cgttcgtgtc ccgctcc                                                    17

<210> SEQ ID NO 17
<211> LENGTH: 21
<212> TYPE: DNA
<213> ORGANISM: artificial
<220> FEATURE:
<223> OTHER INFORMATION: primer

<400> SEQUENCE: 17
ccgcctgagc aaagtaaatg a                                               21

<210> SEQ ID NO 18
<211> LENGTH: 17
<212> TYPE: DNA
<213> ORGANISM: artificial
<220> FEATURE:
<223> OTHER INFORMATION: primer

<400> SEQUENCE: 18
ggcaaccgct ggtttgg                                                    17

<210> SEQ ID NO 19
<211> LENGTH: 24
<212> TYPE: DNA
<213> ORGANISM: artificial
<220> FEATURE:
<223> OTHER INFORMATION: primer

<400> SEQUENCE: 19
tgaaaccttg ggtgtcgttg ggaa                                            24

<210> SEQ ID NO 20
<211> LENGTH: 24
<212> TYPE: DNA
<213> ORGANISM: artificial
<220> FEATURE:
<223> OTHER INFORMATION: primer

<400> SEQUENCE: 20
ttgcgggcca ttgttccatg atga                                            24

<210> SEQ ID NO 21
<211> LENGTH: 31
<212> TYPE: DNA
<213> ORGANISM: artificial
<220> FEATURE:
<223> OTHER INFORMATION: primer

<400> SEQUENCE: 21
```
cgtactttat cggggaaata ggagaagtac g                    31

<210> SEQ ID NO 22
<211> LENGTH: 22
<212> TYPE: DNA
<213> ORGANISM: artificial
<220> FEATURE:
<223> OTHER INFORMATION: primer

<400> SEQUENCE: 22
gtgcttagag aggccgagag ga                              22

<210> SEQ ID NO 23
<211> LENGTH: 24
<212> TYPE: DNA
<213> ORGANISM: artificial
<220> FEATURE:
<223> OTHER INFORMATION: primer

<400> SEQUENCE: 23
atcgaatgga aatgaaagga gtca                            24

<210> SEQ ID NO 24
<211> LENGTH: 22
<212> TYPE: DNA
<213> ORGANISM: artificial
<220> FEATURE:
<223> OTHER INFORMATION: primer

<400> SEQUENCE: 24
gaccattgga tgattgcagt ca                              22

<210> SEQ ID NO 25
<211> LENGTH: 25
<212> TYPE: DNA
<213> ORGANISM: artificial
<220> FEATURE:
<223> OTHER INFORMATION: primer

<400> SEQUENCE: 25
cggaggccga ataggaacag ctccg                           25

<210> SEQ ID NO 26
<211> LENGTH: 23
<212> TYPE: DNA
<213> ORGANISM: artificial
<220> FEATURE:
<223> OTHER INFORMATION: primer

<400> SEQUENCE: 26
gaaatgcaga aatcacccgt ctt                             23

<210> SEQ ID NO 27
<211> LENGTH: 18
<212> TYPE: DNA
<213> ORGANISM: artificial
<220> FEATURE:
<223> OTHER INFORMATION: primer

<400> SEQUENCE: 27
gtttcccagt caggatcc                                   18

<210> SEQ ID NO 28
<211> LENGTH: 68
<212> TYPE: DNA
<213> ORGANISM: homo sapiense

```
<400> SEQUENCE: 28
aaacattggg aatatagtat ttattttggg tgattatgtg tttagttaag tattagagga    60
tattttta                                                             68

<210> SEQ ID NO 29
<211> LENGTH: 51
<212> TYPE: DNA
<213> ORGANISM: Homo sapiens

<400> SEQUENCE: 29 aattttgta gttttagtag agatggagtt ttattatgtt ggttaggttg g              51

<210> SEQ ID NO 30
<211> LENGTH: 36
<212> TYPE: DNA
<213> ORGANISM: Homo sapiens

<400> SEQUENCE: 30
gaaacaggag aatttttga atttgggtgg tagagg                               36

<210> SEQ ID NO 31
<211> LENGTH: 79
<212> TYPE: DNA
<213> ORGANISM: Homo sapiens

<400> SEQUENCE: 31
gaaaatatgg tttgttaatg aatgataggt taattttagt atgttggtta ttttaatatt    60
ttgttattag ttggtttgg                                                 79

<210> SEQ ID NO 32
<211> LENGTH: 54
<212> TYPE: DNA
<213> ORGANISM: Homo sapiens

<400> SEQUENCE: 32
caggtatagt ggtaagaatt tgtagttta gttatttggg aggttgagtt agga           54

<210> SEQ ID NO 33
<211> LENGTH: 68
<212> TYPE: DNA
<213> ORGANISM: Homo sapiens

<400> SEQUENCE: 33
aacttttggt tgggggtggt ggtttatgtt tgtaatttta gtattttggg aggtcaaggt    60
gagtggat                                                             68

<210> SEQ ID NO 34
<211> LENGTH: 47
<212> TYPE: DNA
<213> ORGANISM: Homo sapiens

<400> SEQUENCE: 34
aggtagtttt attttgggtt ttagggaata ggagggaatt agaagga                  47

<210> SEQ ID NO 35
<211> LENGTH: 51
<212> TYPE: DNA
<213> ORGANISM: Homo sapiens

<400> SEQUENCE: 35
cagtattttg ggaggttaag gtaggtggat tatgaggtta ggagattgag a             51
```

```
<210> SEQ ID NO 36
<211> LENGTH: 34
<212> TYPE: DNA
<213> ORGANISM: Homo sapiens

<400> SEQUENCE: 36
gatggattgt ttgagtttag gagtttgaga ttag                              34

<210> SEQ ID NO 37
<211> LENGTH: 60
<212> TYPE: DNA
<213> ORGANISM: Homo sapiens

<400> SEQUENCE: 37
tgagtttagt ttaagttgat tgggtaggta aatgtttgtt atgaatttgg aagtgagaga   60

<210> SEQ ID NO 38
<211> LENGTH: 135
<212> TYPE: DNA
<213> ORGANISM: Homo sapiens

<400> SEQUENCE: 38
caggtgttga gtggtgaggg atgtgtaaat aagtaagtgt ggggttcggt tattgcgtat   60
agttaggtat attggttgtt gtggggtggg gtaggtaatt taagtattag tatgggtatt  120
ggttttttgt gaggc                                                  135

<210> SEQ ID NO 39
<211> LENGTH: 59
<212> TYPE: DNA
<213> ORGANISM: Homo sapiens

<400> SEQUENCE: 39
acaaaaatta gttaggtata gtggtatgta tttgtagttt tagttaatcg ggatcctga    59

<210> SEQ ID NO 40
<211> LENGTH: 46
<212> TYPE: DNA
<213> ORGANISM: Homo sapiens

<400> SEQUENCE: 40
gaatggcaag tattggatta tttacggtcg tggttgtgga tcgata                 46

<210> SEQ ID NO 41
<211> LENGTH: 59
<212> TYPE: DNA
<213> ORGANISM: Homo sapiens

<400> SEQUENCE: 41
gtttgtacgg tgaagtttag gttttattgt ggatacggtt gaaatagaag agtgatggg   59

<210> SEQ ID NO 42
<211> LENGTH: 54
<212> TYPE: DNA
<213> ORGANISM: Homo sapiens

<400> SEQUENCE: 42
tgaacgcggg aggcggagtt tgtagtgagt taagatcgcg ttattgtatt ttag        54

<210> SEQ ID NO 43
<211> LENGTH: 49
<212> TYPE: DNA
<213> ORGANISM: Homo sapiens
```

<400> SEQUENCE: 43
ggaaacgaat gaaattatcg aatggaatcg aatggtgtta tcgaacgga            49

<210> SEQ ID NO 44
<211> LENGTH: 24
<212> TYPE: DNA
<213> ORGANISM: Homo sapiens

<400> SEQUENCE: 44
cggataggag gggttgttat gaag                                       24

<210> SEQ ID NO 45
<211> LENGTH: 36
<212> TYPE: DNA
<213> ORGANISM: Homo sapiens

<400> SEQUENCE: 45
tagttaatta tatgtgttcg ttatttgtgt atgtgg                          36

<210> SEQ ID NO 46
<211> LENGTH: 53
<212> TYPE: DNA
<213> ORGANISM: Homo sapiens

<400> SEQUENCE: 46
atgaaagtgt tttggggatg gatgggggat atggttgtat aatgtggcgg acg       53

<210> SEQ ID NO 47
<211> LENGTH: 110
<212> TYPE: DNA
<213> ORGANISM: Homo sapiens

<400> SEQUENCE: 47
agaatcgttt gagtttagga gtttaagatt agtttgggta atatagtgag attttgttgt    60
tacgaaaata aataaaaaat tagttaggtg tggtggtgta tgtttgtggt             110

<210> SEQ ID NO 48
<211> LENGTH: 60
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n= a, c, g, or t
<220> FEATURE:
<221> NAME/KEY: misc_feature
<222> LOCATION: (21)..(23)
<223> OTHER INFORMATION: n= a, c, g, or t
<220> FEATURE:
<221> NAME/KEY: misc_feature
<222> LOCATION: (54)..(54)
<223> OTHER INFORMATION: n= a, c, g, or t
<220> FEATURE:
<221> NAME/KEY: misc_feature
<222> LOCATION: (56)..(56)
<223> OTHER INFORMATION: n= a, c, g, or t

<400> SEQUENCE: 48
tgtttgttga gtgtacgtnt nnngtatttg tgttgggtgt atgtggatgt gtgngntgag    60

<210> SEQ ID NO 49
<211> LENGTH: 59
<212> TYPE: DNA
<213> ORGANISM: Homo sapiens

<400> SEQUENCE: 49

```
agtttgaagt ttttatagaa gaaggttatg atttattttc ggtaggaagt tttgaagag      59
```

<210> SEQ ID NO 50
<211> LENGTH: 99
<212> TYPE: DNA
<213> ORGANISM: Homo sapiens
<220> FEATURE:
<221> NAME/KEY: misc_feature
<222> LOCATION: (54)..(57)
<223> OTHER INFORMATION: n= a, c, g, or t
<220> FEATURE:
<221> NAME/KEY: misc_feature
<222> LOCATION: (84)..(84)
<223> OTHER INFORMATION: y= t or c

<400> SEQUENCE: 50

```
aggaaagttg gaaggatgag gataacgtag tgttttgttg aagaaggaag agannnngga    60
ttaaattgaa attgattggg tttytaaaat ggatgggat                           99
```

<210> SEQ ID NO 51
<211> LENGTH: 38
<212> TYPE: DNA
<213> ORGANISM: Homo sapiens

<400> SEQUENCE: 51

```
agtttgattt tagattgttg tgttagtaat gagcgagg                             38
```

<210> SEQ ID NO 52
<211> LENGTH: 60
<212> TYPE: DNA
<213> ORGANISM: Homo sapiens
<220> FEATURE:
<221> NAME/KEY: misc_feature
<222> LOCATION: (51)..(51)
<223> OTHER INFORMATION: n= a, c, g or t
<220> FEATURE:
<221> NAME/KEY: misc_feature
<222> LOCATION: (52)..(52)
<223> OTHER INFORMATION: n is a, c, g, or t

<400> SEQUENCE: 52

```
ttatttttat aaaaataaaa aaattagttg ggtgtagtgg cgtatgtttg tngttttagt    60
```

<210> SEQ ID NO 53
<211> LENGTH: 41
<212> TYPE: DNA
<213> ORGANISM: Homo sapiens

<400> SEQUENCE: 53

```
aacgataaag aaaataaaag gagtgaggga ggatagatgg g                         41
```

<210> SEQ ID NO 54
<211> LENGTH: 60
<212> TYPE: DNA
<213> ORGANISM: Homo sapiens

<400> SEQUENCE: 54

```
attagttagg cgtgggggtg ggtgtttgta gttttagtta tttaggaggt tgaggtagga    60
```

<210> SEQ ID NO 55
<211> LENGTH: 133
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n= a, c, g or t
<220> FEATURE:

```
<221> NAME/KEY: misc_feature
<222> LOCATION: (21)..(21)
<223> OTHER INFORMATION: n= a, c, g or t
<220> FEATURE:
<221> NAME/KEY: misc_feature
<222> LOCATION: (33)..(33)
<223> OTHER INFORMATION: n= a, c, g or t
<220> FEATURE:
<221> NAME/KEY: misc_feature
<222> LOCATION: (45)..(45)
<223> OTHER INFORMATION: n= a, c, g or t
<220> FEATURE:
<221> NAME/KEY: misc_feature
<222> LOCATION: (88)..(88)
<223> OTHER INFORMATION: n= a, c, g or t

<400> SEQUENCE: 55
aaggtggggg ttgggggggnt ngttttttcg ggntgttgtc gcggnggagg agcgttttag      60
agtttacggc gtagttttat tcgtcggnat ttaggtggac gttgatcggg ggagagaatt     120
gagtatcggg atc                                                        133

<210> SEQ ID NO 56
<211> LENGTH: 121
<212> TYPE: DNA
<213> ORGANISM: Homo sapiens

<400> SEQUENCE: 56
gagtagagag atgattaaat ttatgttaat tttattattt tggttttgag gttgttgtry      60 aagttttta gaatgtgagt cgggtattgt ttttgaggtt aacgttattt ggtttgcgtt     120
t                                                                    121

<210> SEQ ID NO 57
<211> LENGTH: 57
<212> TYPE: DNA
<213> ORGANISM: Homo sapiens

<400> SEQUENCE: 57
gggaggtagt gatgagagta atagataggg tttaggtgtt tgtgtatgat atgtttg         57

<210> SEQ ID NO 58
<211> LENGTH: 128
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n= a, c, g or t
<220> FEATURE:
<221> NAME/KEY: misc_feature
<222> LOCATION: (60)..(60)
<223> OTHER INFORMATION: n= a, c, g or t
<220> FEATURE:
<221> NAME/KEY: misc_feature
<222> LOCATION: (126)..(126)
<223> OTHER INFORMATION: n= a, c, g or t

<400> SEQUENCE: 58
gatgttatta ataattaga ttatttgtat tcgaattggg taagtagtat aaagganaan      60
gatattatta ataattaga ctatttgtat tcgaattggg taagtagtac aaaggagaag     120 tggggnaa                                                             128

<210> SEQ ID NO 59
<211> LENGTH: 119
<212> TYPE: DNA
<213> ORGANISM: Homo sapiens
```

<400> SEQUENCE: 59

```
tttgtagaag datgtgagag gagaagtgag cggtttata ggtatgatgt tagttataag    60
gggttggtga gttgatgtgg gaggattatt tggtttagga gtttaaggtt gcggtgagt   119
```

<210> SEQ ID NO 60
<211> LENGTH: 153
<212> TYPE: DNA
<213> ORGANISM: Homo sapiens

<400> SEQUENCE: 60

```
tgagggttgg gtttaggata gagtatagag agggagattt agttaggagt ttttttaagg    60
tatatagttt ttgatttta ggtagttaga ataggaacgt ggatatagtt ggtatttaat   120
agacgtatat tagatggata gatttgttat tga                                153
```

<210> SEQ ID NO 61
<211> LENGTH: 108
<212> TYPE: DNA
<213> ORGANISM: Homo sapiens

<400> SEQUENCE: 61

```
tagtagtatg atgttagttt tttttaaatt atagattcaa taaaattcag ttaaaatttt    60
attagtttta tttatttatt gatttagtag agatggatat agtactgt              108
```

<210> SEQ ID NO 62
<211> LENGTH: 224
<212> TYPE: DNA
<213> ORGANISM: Homo sapiens

<400> SEQUENCE: 62

```
gtgttatcgt attggggtta tttgtgtaat taatatgtgt tatttagttt tagggtgtat    60
gtttattgtt ttaattatga tggaggtgta gtttggagat tttgtgttag gagattagta   120
gagtttgggg ttttaagggg atttttgtg ggggagaggg atagttgtgt agtagagtga   180
taatgaaggt ttttgattta atgtgtagtt tttaggttat gtgt                   224
```

<210> SEQ ID NO 63
<211> LENGTH: 112
<212> TYPE: DNA
<213> ORGANISM: Homo sapiens

<400> SEQUENCE: 63

```
atgaaaggtt aaaaattgag atagaagatg tgatttggaa ggttataaga gaagttggat    60
aaagttaaat aaggaaagga atttagaaaa aagtgtttaa tgttgtagaa gg           112
```

<210> SEQ ID NO 64
<211> LENGTH: 112
<212> TYPE: DNA
<213> ORGANISM: Homo sapiens

<400> SEQUENCE: 64

```
atgaaaggtt aaaaattgag atagaagatg tgatttggaa ggttataaga gaagttggat    60
aaagttaaat aaggaaagga atttagaaaa aagtgtttaa tgttgtagaa gg           112
```

<210> SEQ ID NO 65
<211> LENGTH: 75
<212> TYPE: DNA
<213> ORGANISM: Homo sapiens

<400> SEQUENCE: 65

```
ctattcttcc cattctcaac ataactctaa ccttccttca tcctcacacc caacaatcat    60
tcactcattt atcta                                                    75
```

<210> SEQ ID NO 66
<211> LENGTH: 120
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n= a, c, g or t

<400> SEQUENCE: 66

```
gataaagttg tgngtaggga tttttggtag agggaataga aagatggagg tgttgaggta    60
ggagtgatgg gtaggtttga agagtagagt ttagtgtagt gagggggtta ttagtaaggg   120
```

<210> SEQ ID NO 67
<211> LENGTH: 100
<212> TYPE: DNA
<213> ORGANISM: Homo sapiens

<400> SEQUENCE: 67

```
atattttatg gaggagtaat ttttagagta tatgaattgg ttttatggag gaagattgtt    60
atttataggt tggtgtaagt gatggtagta gtggtttgtc                        100
```

<210> SEQ ID NO 68
<211> LENGTH: 59
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n= a, c, g or t

<400> SEQUENCE: 68

```
agaagataag gagaagataa ttattnttt ggtagaggta attgatttga ttattagga     59
```

<210> SEQ ID NO 69
<211> LENGTH: 60
<212> TYPE: DNA
<213> ORGANISM: Homo sapiens

<400> SEQUENCE: 69

```
atgtgtattt aaagtaaggt tatgagattt tggattgttt tttgtttagg atgatatgtg    60
```

<210> SEQ ID NO 70
<211> LENGTH: 41
<212> TYPE: DNA
<213> ORGANISM: Homo sapiens
<220> FEATURE:
<221> NAME/KEY: misc_feature
<222> LOCATION: (32)..(32)
<223> OTHER INFORMATION: n= a, c, g or t

<400> SEQUENCE: 70

```
aagtaaaata attttgtttt tatttatttt anaggattgt t                       41
```

<210> SEQ ID NO 71
<211> LENGTH: 99
<212> TYPE: DNA
<213> ORGANISM: Homo sapiens

<400> SEQUENCE: 71

```
aaaattttaa gattaggtaa aaatattgtg taaagtgaga gggatgtgat ggttaaaaag    60
```

```
tgatttaaga tttttgtaat ttttagttat aatttaaga                              99
```

<210> SEQ ID NO 72
<211> LENGTH: 109
<212> TYPE: DNA
<213> ORGANISM: Homo sapiens

<400> SEQUENCE: 72

```
agataatagt gagtatgata ttttttgttt ttttttattat gtgttaagta ttgtttaggg      60
attaagtggg gttgtgttta ttgtagatgt tgtaggtatg gagttagta                  109
```

<210> SEQ ID NO 73
<211> LENGTH: 188
<212> TYPE: DNA
<213> ORGANISM: Homo sapiens

<400> SEQUENCE: 73

```
atgtatttag ttgtttattg aatattattt taatattgta ttatgaatat tgttatgtta       60
tggattttag gttttattag attggtatta gtatcattta ggaatatttt atgatgtgtg      120
ttgataaatt tttaagataa atgaatttga gatatgtgtg agtattttat aaaataaatt      180
ttgttgga                                                              188
```

<210> SEQ ID NO 74
<211> LENGTH: 56
<212> TYPE: DNA
<213> ORGANISM: Homo sapiens

<400> SEQUENCE: 74

```
atggtttgtt tgttttttgtg gaaaatggta tgaagattgg gtttgtattg aatttg          56
```

<210> SEQ ID NO 75
<211> LENGTH: 70
<212> TYPE: DNA
<213> ORGANISM: Homo sapiens

<400> SEQUENCE: 75

```
tgtagtttta gttatttagg aggttgagat atgagaatta tttgaatttg ggggggggaag     60 gttgtagtga                                                             70
```

<210> SEQ ID NO 76
<211> LENGTH: 210
<212> TYPE: DNA
<213> ORGANISM: Homo sapiens
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (196)..(197)

<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t

<400> SEQUENCE: 76
tgagaagggg gtagtgggga tggttttgtg ggtttatgtt gttttttgatt ttagaaaata    60 aagtttttg taggaagtag gtgggaagta atttgttgat aagtgtaaag atttgggaat    120
tatattaagg ggtaaatgga gganaggtgt tggtgttaan gaggtagacn tatgggagtt   180
nggttttagg aanggnngtg gntagaaagg                                     210

<210> SEQ ID NO 77
<211> LENGTH: 33
<212> TYPE: DNA
<213> ORGANISM: Homo sapiens

<400> SEQUENCE: 77
ggtaggtaga ttatttgagg ttaggagttt aag                                 33

<210> SEQ ID NO 78
<211> LENGTH: 153
<212> TYPE: DNA
<213> ORGANISM: Homo sapiens

<400> SEQUENCE: 78 atatttttt attgaagaat gtagtttttt aaaattaaaa tgtattttta aaatttattt    60
attatttttt gagataaggt tttgttttgt tgtttaagtt agagtatagt atgtgattat   120
agtttattgt agttttgaat ttttgggttt aag                                153

<210> SEQ ID NO 79
<211> LENGTH: 52
<212> TYPE: DNA
<213> ORGANISM: Homo sapiens

<400> SEQUENCE: 79
tgtggggttg ttgttttgag agggttttt tttgggggttt ttattaatga tg            52

METHOD FOR ENRICHING METHYLATED CPG SEQUENCES

CROSS REFERENCE

This application claims priority from U.S. provisional application Ser. No. 61/111,499 filed Nov. 5, 2008, herein incorporated by reference.

BACKGROUND OF THE INVENTION

The task of epigenomic mapping is inherently more complex than genome sequencing since the epigenome is much more variable than the genome. While an individual only has one genome, one's epigenome varies in time and space with age, tissue type, exposure to environmental factors, and shows aberrations in diseases especially in cancer. With methylated CpG's only accounting for ~2-6% of the genome (18), large scale shotgun sequencing efforts will require some form of purification of short CpG methylated sequences. Many current enrichment technologies fall short of the dynamic range necessary to capture minute changes in CpG methylation that can have large repercussions in gene expression.

In the mammalian genome, 60-80% of relatively infrequent (1 per 100 bp on average) CpG dinucleotides are methylated at the carbon 5 position (1). In contrast, dense clusters of unmethylated CpG sequences (~1 per 10 bp) are found at the transcription start sites of genes (2). In certain circumstances, these CpG islands are heavily methylated with the concomitant silencing of the promoter and the silencing of gene activity (3). These modifications are considered to be important for development (4), genomic imprinting (5), and X chromosome inactivation through gene silencing (6, 7). Aberrant DNA methylation of CpG islands has been frequently observed in cancer cells (8).

Many techniques exist for the enrichment of heavily methylated CpG islands from genomic DNA. One protocol relies on methylation-sensitive restriction endonucleases such as HpaII (CCGG) and HhaI (GCGC) followed by PCR identification, Southern Blot analysis or microarray profiling (9). Another approach utilizes the ability of an immobilized methyl-CpG-binding domain (MBD) of the MeCP2 protein to selectively bind to methylated double-stranded DNA sequences. Restriction endonuclease-digested genomic DNA is loaded onto the affinity column and methylated-CpG island-enriched fractions are eluted by a linear gradient of sodium chloride. PCR, microarray, DNA sequencing and Southern hybridization techniques are used to detect specific sequences in these fractions (10). These techniques are limited due to the specific cleavage moiety of the restriction enzyme and therefore will not completely reflect all combinations of bases flanking the methylated CpG dinucleotide.

There are several additional methods for analysis of methylation patterns. In the bisulfite method, single-stranded DNA (ssDNA) is exposed to a deamination reagent (bisulfite) that converts unmethylated cytosines to uracils while methylated cytosines remain relatively intact (11). After cleanup, the resultant treated DNA of interest must be PCR amplified (converting the uracils to thymines) and analyzed by a myriad of techniques that can distinguish between methylated and unmethylated DNA. If the PCR products are cloned and sequenced, alignment analysis of the untreated and treated nucleotide sequences can reveal the in vivo methylation status of the amplified region. The PCR products can also be analyzed by combined bisulfite-restriction analysis (COBRA assay) and methylation-specific PCR (MSP) (12, 13).

Recently, direct shotgun ultra-high-throughput sequencing of bisulfite-converted DNA using the Illumina 1G Genome Analyzer and Solexa sequencing technology have yielded insights of the methylation state of the small (~120 Mbp) genome of the mustard plant *Arabidopsis* (14). This new technology allowed the exact identification and quantification of 5-methylcytosines at the single-nucleotide level in genes. Although highly specific and reasonably sensitive, it required at least 20-fold coverage to theoretically cover all potential methylated cytosines. Currently, no method exists to enrich bisulfite-converted CpG methylated DNA, which by the nature of the deamination reaction, is single-stranded, from total genomic DNA.

SUMMARY

Methods and compositions are described herein that include the embodiments listed below.

In one embodiment, an isolated first polypeptide is provided that includes an amino acid sequence having at least 90% homology or identity with SEQ ID NO:3 and is capable of binding single-stranded methylated polynucleotides. The first polypeptide may be fused to a second polypeptide and may be immobilized on a solid substrate by means of the second polypeptide if the second polypeptide is a substrate-binding domain such as maltose-binding domain (MBP). A property of the isolated first polypeptide may include an ability to bind a methylated CpG in a single-stranded polynucleotide.

Examples of the first polypeptide are human UHRFI, and mouse NP95 SRA. Either of these polypeptides may be used in series or in parallel with a methyl-binding domain (MBD), which binds double-stranded methylated DNA and thus recovery of methylated DNA may be enhanced. For example, the sample may be applied to a MBD column, eluted, denatured and then applied to an SRA column. Additionally, one aliquot of a sample may be applied to an MBD column and one aliquot of sample applied to an SRA column.

The above-described polypeptides either alone or as a fusion protein, either in solution or immobilized on a substrate, may be used for differentially binding a single-stranded methylated polynucleotide to a solid substrate, for example at a CpG site in a low salt solution.

In an embodiment of the invention, a method is provided for enriching for CpG methylated single-stranded polynucleotides from a mixture containing methylated and unmethylated polynucleotides. This method includes: binding the mixture to the first polypeptide described above; eluting the unmethylated polynucleotide from the isolated polypeptide in a solution containing a low concentration of a salt; and eluting the methylated polynucleotide from the isolated polypeptide in a solution containing a high concentration of a salt. The eluted methylated polynucleotide can then be sequenced and the methylation site analyzed.

In embodiments of the invention, a low concentration of the salt is less than 0.4 M salt and a high concentration of the salt is 0.4 M-0.6 M salt. The salt may be, for example, sodium chloride.

In an embodiment of the invention, a method is provided which can be applied to determining the existence of pre-cancerous cells. The method includes: (a) comparing the methylation pattern for selected polynucleotide sequences in both pre-identified transformed eukaryotic cells and non-transformed eukaryotic cells by differential binding of methylated polynucleotides to the first polypeptide of claim 1; (b) determining the presence of abnormal methylation patterns associated with alteration of tumor suppressor function; and (c) utilizing the abnormal methylation patterns as a diagnostic tool for determining whether any eukaryotic cells in a sample are transformed. (In this context "transformed" is intended to mean converted to a pre-cancerous state where the cell is immortalized.)

BRIEF DESCRIPTION OF THE DRAWINGS

FIG. 1A is a chromatogram profile at A280 of human chromatin DNA spiked with a small amount of FAM-labeled methylated (M) and unmethylated (U) CpG-containing oligonucleotides. Both the unmethylated and methylated oligos co-eluted with the bulk of the chromatin DNA between 0.2 M and 0.3 M NaCl.

FIG. 1B shows a gel containing individual column fractions in each lane. At higher NaCl, a faint band (*) on the gel was observed corresponding to single-stranded methylated DNA.

FIG. 1C shows a side-by-side comparison of the methylated and unmethylated oligos confirming that the band (*) corresponded to methylated CpG-containing ssDNA.

FIG. 2A is a comparison of chromatogram profiles at A280 of 100 μg of MseI-digested HeLa DNA spiked with 3 μg of MseI digested M.SssI-labeled $^3$H-Adomet HeLa DNA. The DNA composition was heated to 98° C. for one minute and quickly chilled prior to loading onto the column. A large portion of the $^3$H-labeled DNA eluted off the column at 0.15 M NaCl, however, three distinct peaks that eluted at 0.3 M, 0.35 M and 0.4 M NaCl were observed with a small peak of $^3$H-labeled DNA co-eluted with the 0.4 M NaCl peak. The gel shows the content of each fraction.

FIG. 2B shows the same DNA load preparation, which was sonicated for 1 minute followed by heating of the sample to 98° C. for 1 minute, chilled, and loaded onto the column. Three peaks were observed at 0.35 M, 0.4 M and 0.45 M NaCl with the bulk of the $^3$H-labeled DNA co-eluted with the 0.4 M and 0.45 M peaks, respectively. The gel shows the content of each fraction.

FIGS. 4A-4B show a comparison of two chromatogram profiles at A280 of 100 μg of sonicated, heated HeLa genomic DNA FIG. 4A or 200 μg initial concentration of sonicated, bisulfite-converted genomic DNA FIG. 4B. The 0.3 M and 0.5 M fractions were characterized by qRT-PCR or cloned and sequenced.

FIG. 4C shows the bisulfite-converted fractions which were labeled and extended with a random "fourN" oligonucleotide, and PCR amplified. Ethidium-stained 20% TBE polyacrylamide gel analysis of the PCR products before (−) and after (+) BamH1 treatment showed the size distribution of fragments from the two peaks.

FIG. 4D shows GST-SRA-domain coupled magnetic beads only retained methylated (M) ssDNA lambda DNA after extensive washing with 0.3M NaCl as assayed on an ethidium-stained 20% TBE polyacrylamide gel.

FIG. 7 shows the DNA sequences of mouse and human (SEQ ID NOS:4 and 5, respectively).

FIG. 8 shows how SRA domain can be used in sequencing platforms (e.g. Helicos sequence platform) to detect methylated CpG DNA. 1. Methylated ssDNA (SEQ ID NO:6) annealed to polyT on a slide. 2. Methylated cytosine detected by fluorescence labeled NP95 SRA domain and 3. SRA is washed off. DNA is sequenced. Within the flow cells, billions of single molecules of ssDNA are captured on a solid surface. These captured strands serve as templates for the sequencing-by-synthesis process. Prior to the addition of polymerase and one fluorescently labeled nucleotide (C, G, A or T), the cell is flooded with MBP-SRA domain protein, which binds specifically to methylated CpG sequences. The cell is washed with a 100 mM NaCl wash buffer, and fluorescently labeled Anti-MBP antibody couples to the MBP-NP95 SRA domain/methylated CpG DNA complexes. After a wash step, which removes free Anti-MBP antibody, the cell is imaged and the positions of the methylated CpG-containing DNA strands are recorded. A high wash step (500 mM NaCl) removes the Antibody-MBP-NP95 SRA domain and the sequencing process continues with a polymerase catalyzing the sequence-specific incorporation of fluorescent nucleotides into nascent complementary strands on all the templates. Multiple cycles result in complementary strands greater than 25 bases in length synthesized on billions of templates, providing a sequence read on the methylated CpG templates.

DETAILED DESCRIPTION OF EMBODIMENTS

Figure 6:
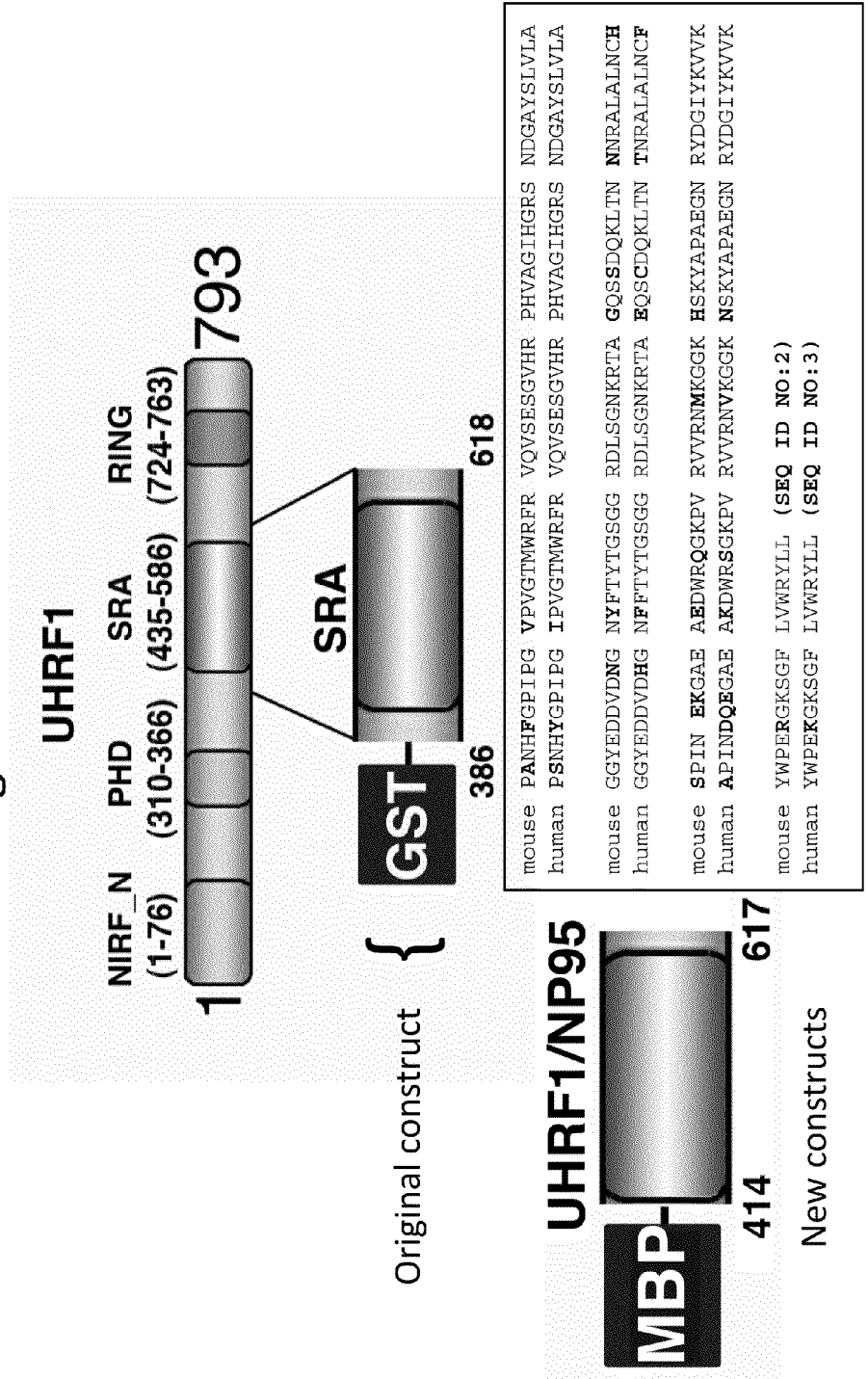
FIG. 6 shows a cartoon of the UHRFI gene illustrating the location of the different domains in the protein. The inset shows an amino acid alignment of the SRA domains from mouse and human (SEQ ID NOS:2 and 3, respectively), revealing that the sequences are 90% identical.

UHRFI is a ubiquitin-like protein that improves fidelity of maintenance of methylation and has a histone methyltransferase function. It contains multiple domains (see FIG. 6). Two adjacent domains in the protein are named SET and RING and together are called the SRA domain. The SRA domain has a sequence shown in FIG. 7. The SRA domain is capable of binding methylated CpG in a salt-dependent manner. In an embodiment of the invention, the SRA is immobilized on a matrix and can be used to bind methylated and unmethylated ssDNA or bisulfite-converted genomic DNA at low salt conditions (for example 0.15 M NaCl). The unmethylated DNA can be eluted from the SRA protein in conditions of increased salt concentration such as 0.3 M NaCl while methylated DNA can be eluted at 0.5 M NaCl.

Human UHRFI is an example of a family of DNA-binding proteins that are associated with regulating gene expression via methylation. Other example include DNMTI and mouse NP95 SRA. This family of related proteins are shown here to be effective in differentiating methylated from unmethylated DNA.

These proteins can be produced in high yield and are relatively stable, which makes them suitable for attaching to solid substrates such as agarose resin or carbohydrate-coated beads or magnetic beads (NEB) without loss of binding activity. The immobilized protein can easily be integrated in a high-throughput bisufite sequencing setup. With just one wash step, mild elution characteristics, sensitivity and accuracy are enhanced. Thus, the reusable matrix provides valuable information on the methylome, providing insights into aging and disease.

There are a variety of approaches by which the SRA-like proteins can be immobilized on a matrix. The matrix may include beads, 96 well plastic dishes, columns or any other support material. Where beads are selected, these can be magnetic, colored and/or coated with a carbohydrate or other ligand suitable for binding the SRA. To facilitate binding of the SRA-like proteins to a matrix, the SRA-like protein can be synthesized as a fusion protein by standard molecular biology techniques in prokaryotic or eukaryotic host cells. For example, the SRA-like proteins may be synthesized as SRA-chitin-binding domain for binding chitin or SRA-MBP for binding to amylose. Examples of suitable fusion proteins are provided for example in U.S. Pat. No. 5,643,758.

Other examples of fusion proteins include SRA-AGT or SRA-ACT proteins (using the SNAP-tag™ or CLIP-tag™ technology provided commercially by New England Biolabs). These fusion proteins can be labeled as required for detection of purification of polynucleotides for example by using fluorescent labels after covalent binding of the ACT/AGT in the fusion protein to labeled substrates such as benzyl guanine or benzyl cytosine, leaving available the SRA to bind methylated DNA in vitro or in vivo.

The SRA may also be bound to a matrix or solid substrate such as beads, columns, glass, plastic or polymer surfaces, etc. Binding can be achieved by any ligand/ligand-binding molecule system including antibody/antigens or biotin/strepavidin, chitin-binding domain, maltose-binding domain, etc. SRA-like proteins may be synthesized as intein fusions to facilitate certain separation methods (U.S. Pat. Nos. 5,496,714 and 5,834,247).

In an embodiment of the invention, a binding preference for methylated single-stranded polynucleotides by SRA-like proteins was demonstrated. This property can be exploited for detection, purification and analysis of the polynucleotides using immobilized SRA bound to the matrix. The methylated polynucleotides can then be sequenced to identify the location of the methylated CpG. In another embodiment, a double stranded polynucleotide can be bound to SRA where methylation if present can be detected on one strand or the other.

Mammalian UHRF1 SRA domains (such as human UHRF1 or murine NP95) can be used to augment high-throughput sequencing methodologies, for example, True Single Molecule Sequencing (tSMS)™ technology (Helicos Biosciences) by binding and identifying single-stranded methylated CpG-containing DNA prior to a series of nucleotide additions and detection cycles that will then determine the sequence of each fragment (FIG. 8). By integrating the UHFR1-SRA domain into this instrumentation setup, additional epigenetic information can be layered on top of rapid and inexpensive resequencing of genomes to facilitate the understanding of methylation states in complex organisms.

The mammalian UHRF1 SRA domains can be displaced from the polynucleotide by adding cations that neutralize the charge on the DNA and thereby release the electrovalently bound protein. In embodiments of the invention, the protein binding to the polynucleotide is disrupted using NaCl. However, the use of this salt is not intended to be limiting. Moreover, it was found that protein binds to polynucleotide at methylated CpGs more tightly so that a high salt concentration was required to release CpG methylated polynucleotides and a low salt concentration was required to release CpG unmethylated polynucleotides. In an embodiment of the invention, the low salt concentration was 0.3 M NaCl whereas the high salt concentration was 0.5 M NaCl. Table 1 provides the results of a two-step salt gradient.

Table 1 shows a sequence analysis of the two NaCl peaks from the GST-SRA-domain column. Greater than 10-fold enrichment of methylated CpG-containing DNA was observed. 19/30 reads with an average size of 63 bases in the high (0.5 M) NaCl fraction contained at least one methylated CpG. 44/1900 bases were methylated CpG or 2.32% of the total. 3/22 reads with an average size of 105 bases in the low salt 0.3M peak contained methylated CpG. 5/2327 bisulfite-converted bases were identified as methylated CpG or 0.215% of the total.

EXAMPLES

Example 1

SRA-Domain Protein Purification and the Covalent Coupling of the Protein to Solid-State Matrixes The SRA domain (386-618) was amplified from full-length human UHRF1 cDNA synthesized using total RNA from HeLa cells. The product was cloned into pENTR-TEV (GST Tag Invitrogen) and recombined into pDEST15 (Invitrogen, Carlsbad, Calif.) to create the GST fusion. The construct was propagated in T7 Express *E. coli* (NEB) to an OD 590 of 0.5 at 37° C. and induced with 0.1 mM IPTG overnight at 16° C. Cells were spun, broken open by French press, spun again and the supernatant layered over a 10 ml Glutathione Separase High Performance column (GE Healthcare). After a 10-column wash, the protein was eluted with a 10 mM L-Glutathione (Sigma) solution. The yield was 12 mg total of purified SRA-domain from 8 liters shake flasks.

GST-SRA Column

9 µls of 1.2 mg/ml (10.8 mg total) of previously purified and dialyzed GST-SRA-domain protein in 10 mM Tris pH. 7.5, 1 mM EDTA and 0.2 M NaCl was layered onto a 4.5 ml Glutathione Sepharose matrix equilibrated with the above buffer. Of the 10.8 mg load, 7.83 mg remained bound to the column. The resin was washed with 10 column volumes of the above buffer, then cycled twice with the above buffer supplemented with 1 M NaCl before final equilibration at 0.05 M NaCl. Sequences of the methylated oligonucleotides were FAM-GTAGG5GGTGCTACA5GGTTCCTGAAGTG top strand (SEQ ID NO:7), FAM-CACTTCAGGAAC5GTGTAGCAC5GCCTAC bottom strand with 5=5 methyl cytosine. Sequences of the unmethylated oligonucleotides were GTCACTGAAGCGGGAAGG-GACTGGCTGCTCCCGGGCGAAGTGCCGGGG CAG-GATCT-FAM top strand (SEQ ID NO:8), AGATCCTGCCCCGGCACTTCGCCCGG-GAGCAGCCAGTCCCTTCCCGCTT CAGTGAC-FAM bottom strand.

qPCR Analysis of NaCl Fractions From GST-SRA-Column

DNA from the high and low salt fractions were characterized by real-time PCR on a Bio-Rad MyiQ iCycler using Bio-Rad iQ SYBR Green Supermix and the following primer sets: hsALDOA TCCTGGCAAGATAAGGAGTTGAC forward (SEQ ID NO:9), ACACACGATAGCCCTAGCAGTTC reverse (SEQ ID NO:10), hsSERPINA GGCTCAAGCTG-GCATTCCT forward (SEQ ID NO:11), GGCTTAATCACG-CACTGAGCTTA reverse (SEQ ID NO:12), hsRPL30 CAAGGCAAAGCGAAATTGGT forward (SEQ ID NO:13), GCCCGTTCAGTCTCTTCGATT reverse (SEQ ID NO:14), hsRASSF1 TCATCTGGGGCGTCGTG forward (SEQ ID NO:15), CGTTCGTGTCCCGCTCC reverse (SEQ ID NO:16), hsMYO-D CCGCCTGAGCAAAGTAAATGA forward (SEQ ID NO:17), GGCAACCGCTGGTTTGG reverse (SEQ ID NO:18), hsMYT1 TGAAACCTTGGGT-GTCGTTGGGAA forward (SEQ ID NO:19), TTGCGGGC-CATTGTTCCATGATGA reverse (SEQ ID NO:20), rDNA CGTACTTTATCGGGGAAATAGGAGAAGTACG forward (SEQ ID NO:21), GTGCTTAGAGAGGCCGAGAGGA reverse (SEQ ID NO:22), hsSAT ATCGAATGGAAAT-GAAAGGAGTCA forward (SEQ ID NO:23), GACCATTG-GATGATTGCAGTCA reverse (SEQ ID NO:24), LINE CGGAGGCCGAATAGGAACAGCTCCG forward (SEQ ID NO:25), GAAATGCAGAAATCACCCGTCTT reverse (SEQ ID NO:26). Cycle program was as follows: cycle 1: (1×) 95° C., 5 minutes, cycle 2 (40×) step 1: 95° C. 10 seconds, step 2: 61° C. 30 seconds, step 3 72° C. 30 seconds.

Cloning and Sequencing of NaCl DNA Fragments from GST-SRA-Column

Eluted and de-salted DNA fragments were cloned into BamH1 cut and alkaline phosphatase (CIP) treated LITMUS 28i cloning vector using the "fourN" procedure (17) with the exception of the sequence of the oligonucleotide: GTTTC-CCAGTCAGGATCCNNNN (SEQ ID NO:1) and PCR primer GTTTCCCAGTCAGGATCC (SEQ ID NO:27). PCR products were purified using Qiagen columns cut with BamH1, purified again, ligated to the vector and cloned as stated.

Results

Figure 1:
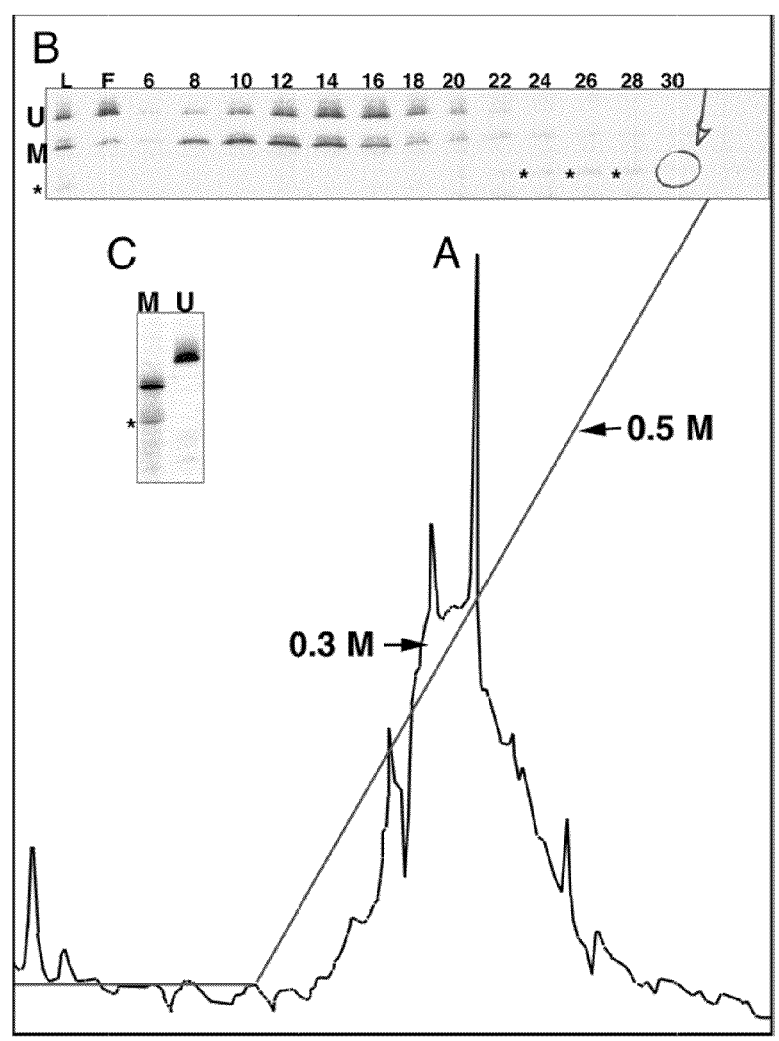
FIGS. 1A-1C show a GST-SRA-domain resin with bound and eluted methylated, and unmethylated dsDNA at low NaCl; and eluted methylated ssDNA at high NaCl.

GST-SRA-Domain of Human UHFR1 Coupled to a Solid Matrix Enriched Single-Stranded Methylated CPG-Containing DNA To determine the preference of the SRA-domain for unmethylated, fully methylated or hemi-methylated double-stranded or ssDNA in a solid state matrix, the following experiment was performed. 7.83 milligrams of purified GST-SRA domain was bound to a 4.5 ml GST column. 1.68 milligrams of MNase digested chromatin (~150-1000 bp) from human Jurkat cells spiked with 1 µg each of fluorescein (FAM)-labeled double-stranded methylated CpG oligonucleotide and unmethylated CpG oligonucleotide of different sizes were layered onto the column in buffer A (10 mM Tris pH. 7.5, 1 mM EDTA, 0.05 M NaCl). After a 10 volume column wash with buffer A, the column was developed with a 100 ml NaCl gradient to 1 M and the fractions were assayed by gel electrophoresis (FIGS. 1A-1C). Both the methylated and unmethylated DNA oligos co-eluted with the bulk of the chromatin DNA between 0.2 M and 0.3 M NaCl. Interestingly, a faint fluorescent band that was smaller than the two annealed oligos was eluted off the column at ~0.4 M NaCl. It was speculated that this band might contain unannealed methylated ssDNA.

Figure 2:
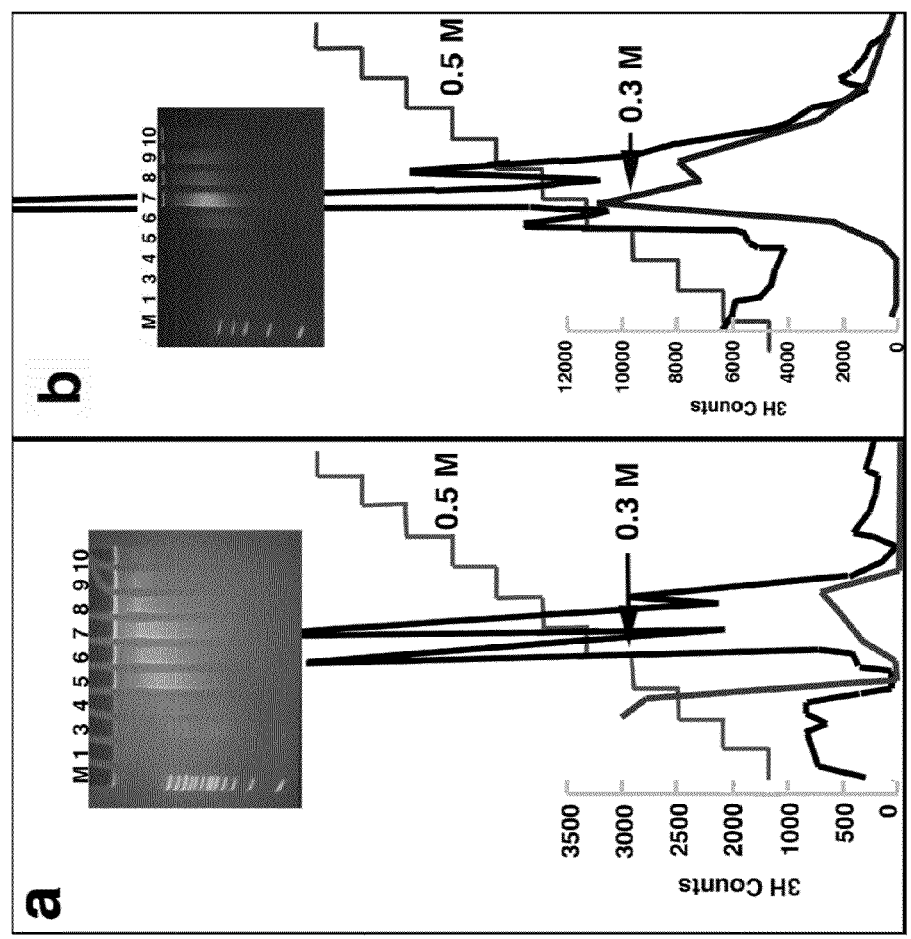
FIGS. 2A-2B show a DNA preparation with significantly altered elution characteristics of the GST-SRA-domain column.

To further investigate the binding preferences of the SRA-domain resin for ssDNA, 100 µg of MseI-digested HeLa DNA spiked with 3 µg of MseI-digested M.SssI-labeled $^3$H-Adomet HeLa DNA was applied to the above equilibrated GST-SRA domain column. After column wash in buffer A, a 30 ml step gradient from 0.1 M to 0.6 M NaCl was initiated and fractions collected. The double stranded DNA and the $^3$H-labeled fully methylated double-stranded DNA eluted off the column in the first two fractions at 0.15 M NaCl. Next, another DNA preparation of the same composition was heated to 98° C. for 1 minute and quickly chilled on ice for 5 minutes prior to loading on the equilibrated column. The above step gradient was used to elute the DNA and the fractions were analyzed as before. A large portion of the $^3$H-labeled DNA eluted off the column at 0.15 M NaCl; however, three distinct peaks that eluted at 0.3 M, 0.35 M and 0.4 M NaCl were observed with a small peak of $^3$H-labeled DNA co-eluted with the 0.4 M NaCl peak. Finally, a third DNA load preparation was sonicated for 1 minute followed by heating of the sample to 98° C. for 1 minute, chilled, and loaded onto the column. Three peaks were observed at 0.35 M, 0.4 M and 0.45 M NaCl with the bulk of the $^3$H-labeled DNA co-eluted with the 0.4 M and 0.45 M peaks, respectively (FIGS. 2A and 2B). It was concluded that sonication plus heating of the sample fully fractionated the genomic DNA into a single-stranded form that facilitated binding of the DNA to the resin and greatly improved the resolving power of the matrix to discriminate between unmethylated and fully methylated CpG DNA.

Simplified Elution Profile Enriched Active and Inactive Genes

Figure 5:
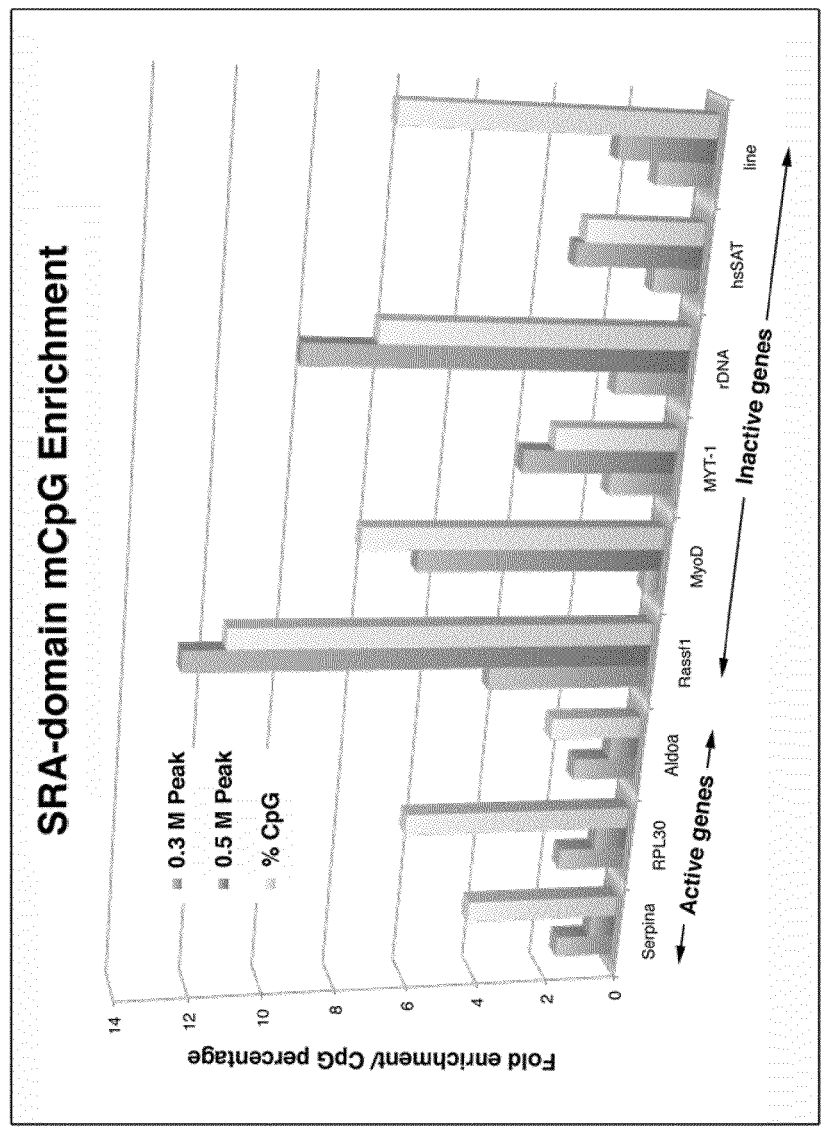
FIG. 5 shows active and inactive gene enrichment from GST-SRA-domain column. Active genes showed at least a 2-fold enrichment over input DNA in the 0.3 M peak. Single copy inactive genes showed a direct correlation of the fold enrichment and CpG occupancy in the 0.5 M peak. As the copy number increased, satellite and line elements showed an inverse correlation between CpG occupancy and enrichment.

A new DNA preparation containing 100 µg of sonicated, heated HeLa genomic DNA was layered onto the above equilibrated column in buffer A. To simplify the elution protocol, a 0.15 M wash step and a 0.3 M and 0.5 M elution steps were employed. Fractions containing the 0.3 M and 0.5 M peaks were collected, desalted and concentrated using a Qiagen miniprep column (FIG. 3 flow chart and FIGS. 4A-4D). The products from the salt fractions were characterized by qPCR on a BioRad iCycler using primers to known active and inactive genes in HeLa cells (FIG. 5). The actively transcribed genes Aldolase A (ALDOA), serpin peptidase inhibitor (SERPINA) and 60S ribosomal protein L30 (RPL30) showed a consistent two-fold enrichment in the 0.3 M peak over input DNA. The high salt peak, presumably containing the inactive gene fraction, revealed little or no enhancement of these genes.

Six known repressed areas of the HeLa genome were interrogated in a similar fashion. Single-copy genes RAS association domain family protein 1 (RASSF1), myogenic differentiation 1 (MYO-D), and myelin transcription factor 1 (MYT1) as well as tandem repetitive ribosomal DNA (rDNA) showed a direct correlation of fold enrichment and CpG occupancy in the 0.5 M peak. Highly repetitive satellite DNA (hsSAT) showed less enrichment in the high salt peak. In spite of high CpG content, long interspersed nuclear (LINE) elements that are transcribed by RNA polymerase II into mRNA (16) showed little difference between the low and high salt fractions, suggesting that the SRA-domain column may accurately reflect the extent of methylation of these sequences in the genome.

Random Sequencing of Cloned Fragments Derived from NaCl Eluted Fractions

Figure 3:
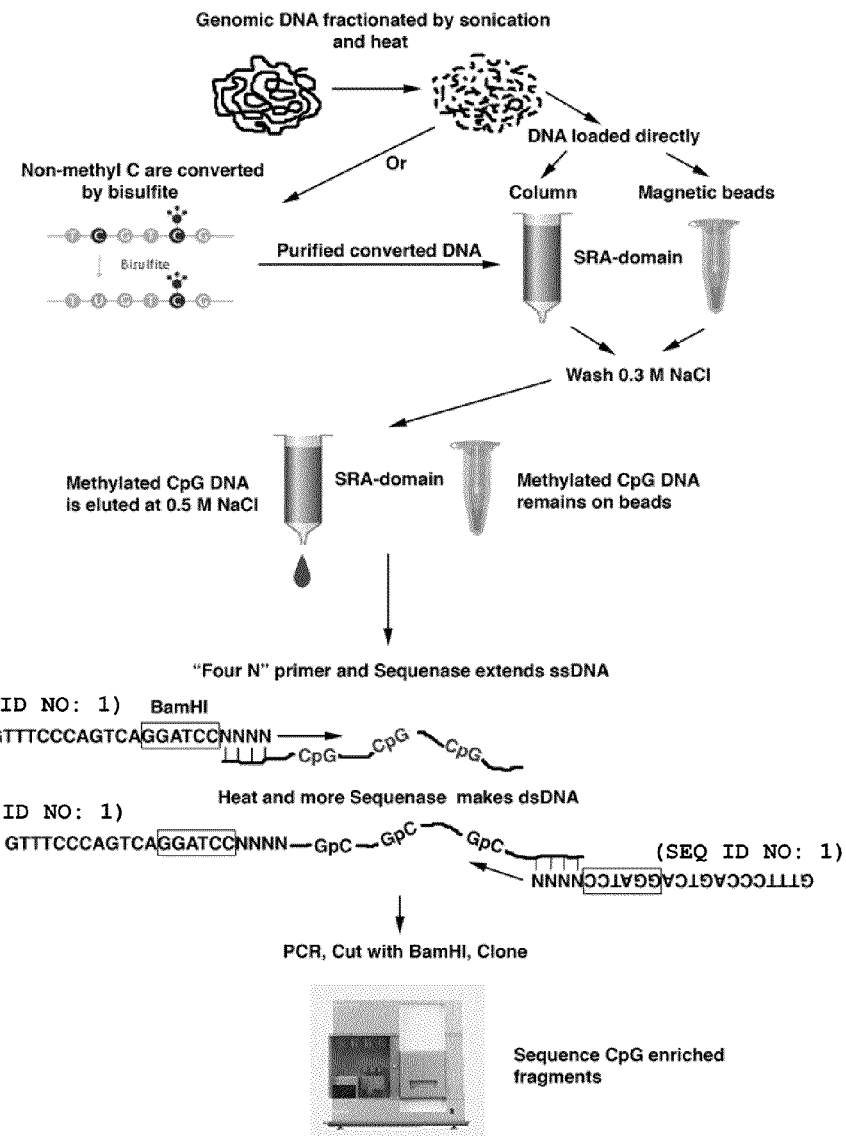
FIG. 3 shows a flowchart of the procedures used to enrich single-stranded methylated CpG-containing DNA. Total genomic DNA was sonicated to 50-150 base fragments. The sample was heated to 98° C., chilled and loaded onto the GST-SRA-domain column (or magnetic beads), or bisulfite-converted (which made the sample single-stranded and converted all non-methyl cytosines to uracils) prior to loading. The column/beads were washed with buffer containing 0.3 M NaCl, which eluted the active gene fraction. Methylated CpG-containing DNA remained on the column matrix and can be eluted with 0.5 M NaCl or alternatively equilibrated with low NaCl buffer prior to the addition of the "fourN" cloning/sequencing primer (SEQ ID NO:1). The sample was heated to 98° C., chilled to 4° C., and then slowly raised to 37° C. Sequenase was introduced into the reaction, allowed to extend the ssDNA fragments, heated and chilled, with more Sequenase added to label the other end of the DNA fragment. The defined-ends DNA was further amplified by a complementary PCR primer without the random nucleotides, purified and digested with BamH1, purified and cloned into a sequencing vector.
Figure 4:
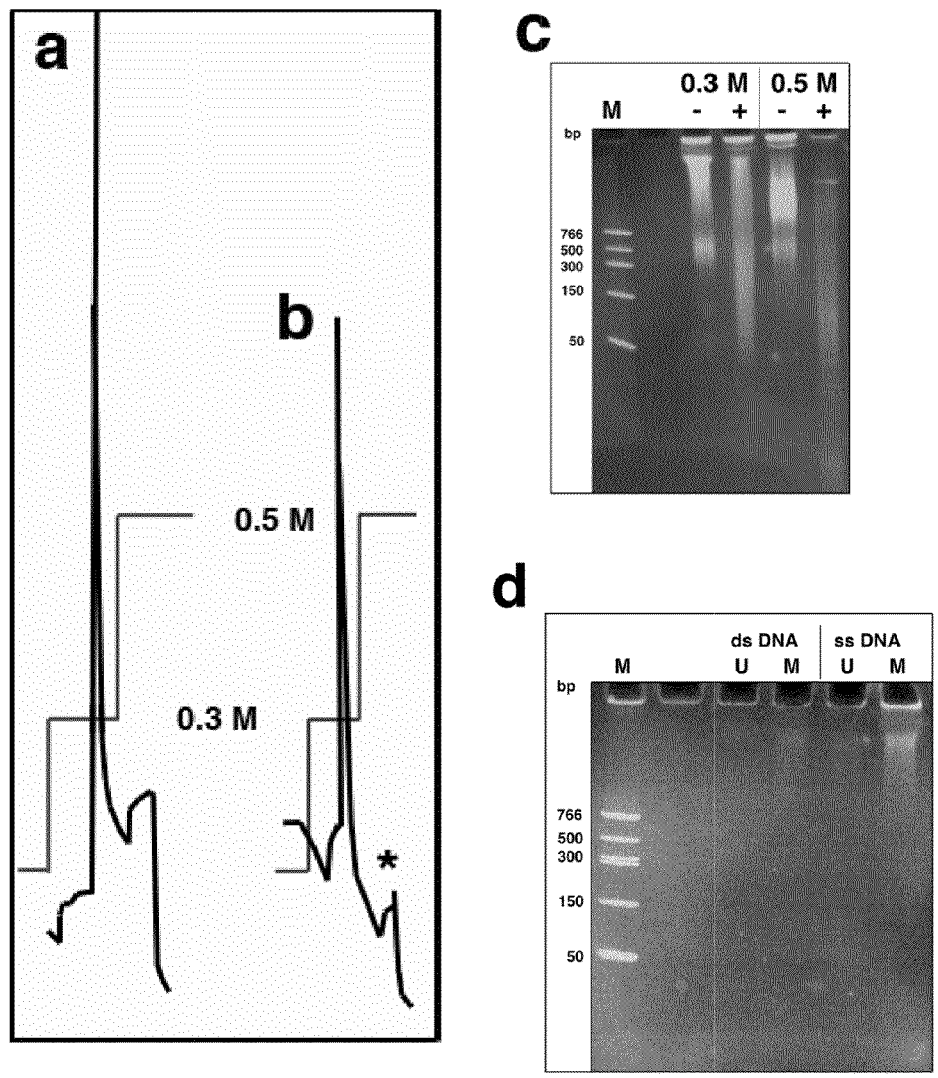
FIGS. 4A-4D show a simplified step salt gradient of GST-SRA-domain column yielded reproducible elution profiles.

Sodium bisulfite conversion of genomic DNA, while highly degrading as a consequence of the reaction, can yield very high-resolution information about the methylation state of a given segment of DNA. As the SRA-domain resin favored fragmented ssDNA, it was ideally suited to bind and resolve bisulfite-converted DNA. To explore the characteristics of the SRA-domain column when bisulfite DNA is applied, 200 µg of HeLa genomic DNA converted by the Epitect Bisulfite Kit (Qiagen) was applied to the equilibrated column, washed and eluted as before. As in previous runs, two peaks were observed at the 0.3 M and 0.5 M NaCl step elutions. Fractions were collected, concentrated and de-salted by Qiagen columns. Cloning of the fragments was accomplished using a modification of the "fourN" procedure (17) in which a small oligonucleotide containing four random bases followed by a BamHI restriction site were annealed to the fragments at both ends and extended with Sequenase. Primers complementary to known sequences introduced during the random priming reaction were added and a PCR reaction amplified the products. After cleavage with BamHI restriction enzyme, the DNA was cloned into a BamHI linearized Litmus 28i vector and plated on AMP/IPTG/XGAL plates (FIG. 3 flow chart).

The DNA from 100 white colonies of the 0.5 M peak and 50 colonies of the 0.3 M peak were submitted for sequencing. Of those 100 reads from the 0.5 M peak, 30 were deemed suitable for analysis by the following criteria: 1) Contained viable sequences that could be identified by NCBI BlastN as human; 2) Showed evidence of non-methyl cytosine conversion (C to T or G to A, depending on orientation); and 3) unconverted C that was followed by G or unconverted G followed by C, again depending on forward or reverse sequencing orientation. Out of these 30 reads (Table 1) with an average size of 63 bases, 19 contained at least one methylated CpG. Of the 1900 bases sequenced, 44 were methylated CpG or 2.32% of the total. Amazingly, out of the 19 methylated CpG sequences, 10 mapped to known CpG methylation sites: nuclear receptor subfamily 4 (19), Fanconi anemia (20), von Willebrand factor (21), coagulation factor XIII and transglutaminase (22), chromodomain protein Y-like (23), spectrin repeat (24), HECTD1 (25), zinc finger and BTB domain containing 46 (26), and pumilio (27). Out of 22 reads with an average size of 105 bases in the low salt 0.3M peak, 3 contained methylated CpG. Of these 2327 bisulfite-converted bases, 5 were identified as methylated CpG or 0.215% of the total. Although limited in scope, these data showed a better than 10-fold enrichment of methylated CpG from the high NaCl peak versus the low NaCl peak. Additional sequencing efforts will be required to fully determine the potential fold enrichment by the SRA-domain resin as compared to random sequencing of genomic DNA or to CpG methylated DNA that was augmented by other means such as an MBD column.

GST-SRA-Domain Protein Covalently Coupled to Magnetic Beads Showed Similar Binding and Elution Characteristics An alternative to column chromatography, GST-SRA-domain protein covalently coupled to a nonporous paramagnetic particle was tested for its suitability as a high-throughput purification matrix for methylated CpG sequences. To compare the binding characteristics of the GST-SRA-domain magnetic beads, 5 µg of sonicated unmethylated lambda DNA or 5 µg of sonicated fully enzymatically methylated (M.SssI) lambda DNA was added to a 50 µl of a 50% slurry of 10 mg/ml SRA-domain magnetic beads in 150 mM NaCl, 0.1% Tween 20, 10 mM Tris pH 7.5, and 1 mM EDTA and allowed to mix end over end for 30 minutes at room temperature. The tubes were placed on a magnetic separation rack and the supernatant was aspirated. The samples were washed and magnetically separated three times by the above buffer supplemented with 150 mM NaCl. The beads were then loaded directly on a 20% native TBE acrylamide gel for analysis. Similarly, sonicated methylated and unmethylated lambda DNA samples were heated to 98° C. and chilled prior to binding on the magnetic beads, followed by washes as stated above. Based on the ethidium stained DNA gel, it was determined that only the methylated heated lambda DNA remained on the beads after the 0.3 M NaCl washes (FIGS. 4A-4D). Additional work is needed to characterize the DNA fragments that remain bound to the beads by direct linker addition and DNA sequencing.

Example 2

Common Properties Shared by Sra Domains from Different Sources

MBP-NP95 SRA-domain fusion protein effectively enriched single-stranded methylated CpG DNA using a small amount of input DNA. This was demonstrated as described below.

The SRA domain of mouse NP95, which is 90% identical to human UHRF1, bound and enriched fragmented methylated ssDNA using 1 µg of input DNA. In addition, mouse NP95 SRA domain purified methylated CpG-containing DNA by 20-25 fold from 1 µg of fractionated ssDNA, and was comparable to methyl binding domain in yield and sensitivity.

Figure 9:
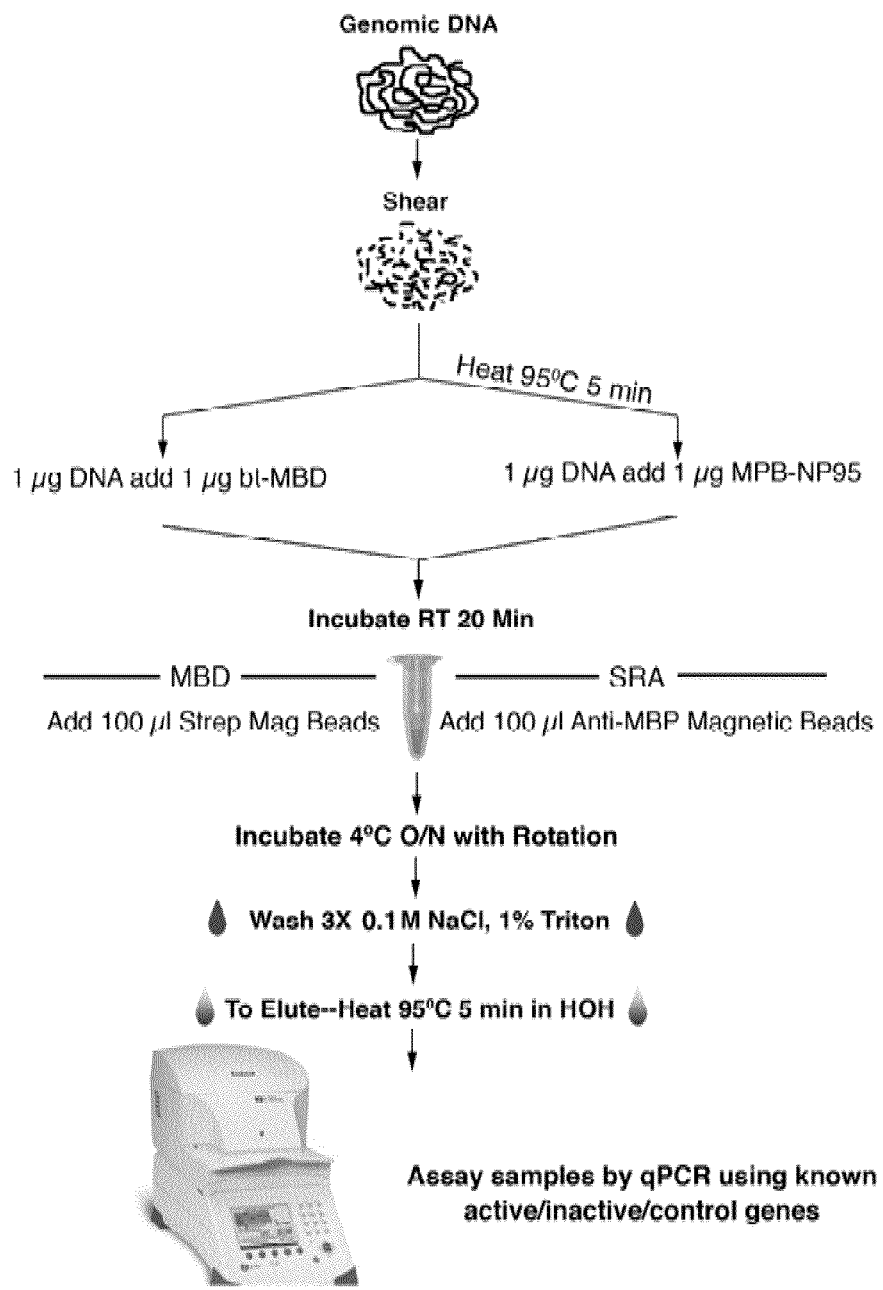
FIG. 9 shows a flowchart of the procedure used to compare a commercially available methylated CpG DNA enrichment system (e.g. Invitrogen) with MBP-NP95 SRA domain. Total HeLa genomic DNA was sonicated to 50-150 base fragments. Half of the sample was heated to 95° C. for 5 minutes and chilled on ice. The other half of the sample was not heated. To 1 μg of unheated sample, 1 μg of biotinylated (bt) MBD and buffer were added. Similarly, to 1 μg of heated DNA, 1 μg of MBP-NP95 SRA domain and buffer were added. Both samples were incubated at room temperature for 20 minutes. To the bt-MBD sample 100 μl (1 mg) of Streptavidin Magnetic Beads was added. To the MBP-NP95 SRA domain sample 100 μl (1 mg) of Anti-MBP Magnetic Beads was added. The samples were then incubated overnight at 4° C. with rotation. The bound complexes were then washed 3× with 100 mM NaCl, 1% Triton, 0.1% Tween buffer, with magnetic separation and aspiration of buffer and 1× with TE buffer containing 0.1% Tween. Finally, a small quantity of water was added to the aspirated samples, and the enriched methylated DNA complexes were eluted from the magnetic beads by heat. The complexes were then assayed by qPCR using primer sets to known active and inactive genes in HeLa DNA.
Figure 10:
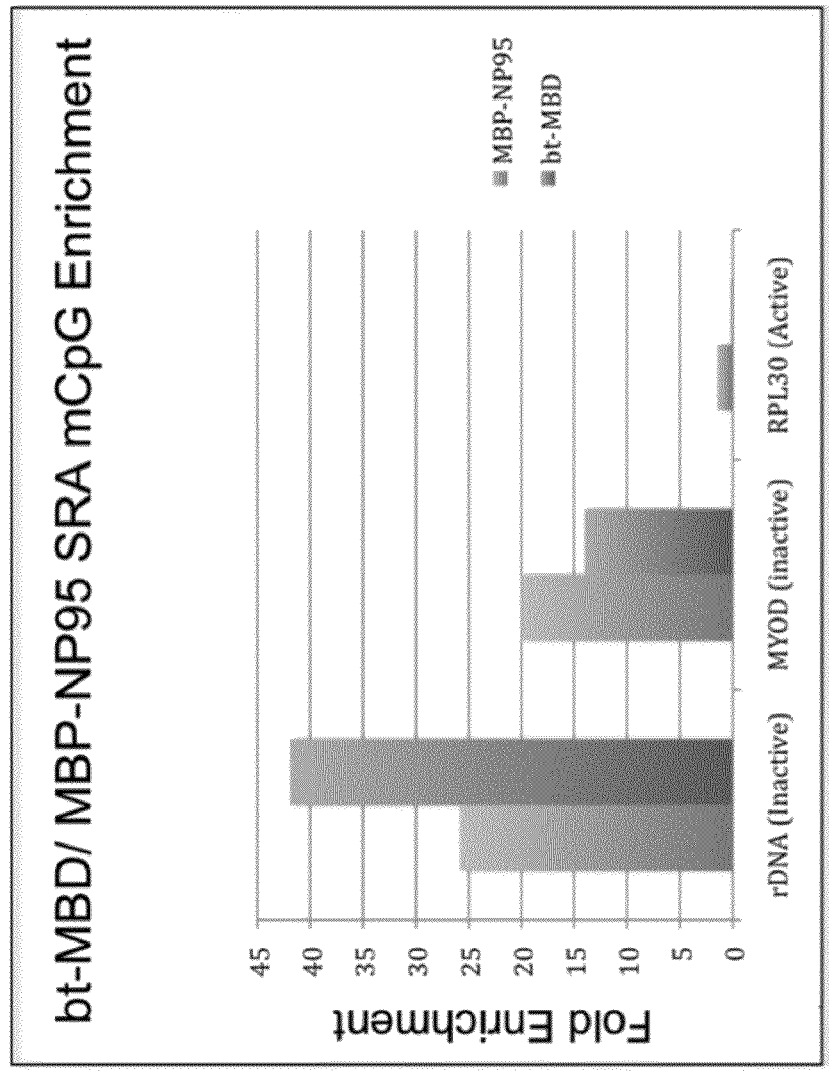
FIG. 10 shows the number of fold enrichment values of known methylated (inactive) and unmethylated (active) genes comparing a commercially available methyl CpG enrichment system (e.g. Invitrogen) with MBP-NP95 SRA domain protein. Both techniques resulted in similar enrichment of the inactive genes rDNA and MYOD, with no enrichment of the active gene RPL30.

An alternative to column chromatography, a MBP-NP95 SRA-domain fusion protein in conjunction with Anti-MBP monoclonal antibody coupled to a paramagnetic bead was tested for its suitability as a high-throughput purification matrix for methylated CpG sequences. To compare the binding and elution characteristics of the NP95 SRA-domain with a commercially available methylated CpG enrichment system employing biotinylated MBD (MethylMiner™ Methylated DNA Enrichment Kit from Invitrogen), 1 µg of sonicated, heated HeLa DNA (NP95 SRA) and 1 µg of sonicated HeLa DNA (MBD) was added to 1 µg of MBP-NP95 SRA (15 µl) or 1 µg of biotinylated MBD (2 µl), in a 200 µl total reaction mix containing 20 µl 10× NEBuffer 4 (50 mM potassium acetate, 20 mM Tris-acetate, 10 mM magnesium acetate, 1 mM dithiothreitol pH 7.9) and 2 µl 100 µg/ml BSA was incubated for 30 minutes at room temperature. To the MBP-NP95 SRA reactions, 100 µl (1 mg) of Anti-MBP magnetic beads (NEB) was added. To the MBD reactions, 100 μl (~1 mg) of streptavidin magnetic beads (Invitrogen) was added. Both reactions were allowed to mix end over end over night at 4° C. The tubes were placed on a magnetic separation rack and the supernatant was aspirated. The samples were washed and magnetically separated 3× by 15 ml of wash buffer (20 mM Tris-HCl pH 7.5, 100 mM NaCl, 1 mM EDTA, 1% Triton X-100, 0.1% Tween 20) followed by a final 15 ml wash in low salt buffer (20 mM Tris-HCL, 1 mM EDTA, 0.1% Tween 20 (see FIG. 9). 140 μl of water was added to the bead complexes and the DNA samples were heated to 98° C. to liberate the enriched methylated DNA. The products from this heat step were characterized by qPCR on a BioRad iCycler using primers to known active and inactive genes in HeLa cells. The actively transcribed gene ribosomal protein L30 (RPL30) showed no enrichment in the MPB-NP95 SRA samples or the bt-MBD samples. The methylated genes myogenic differentiation 1 (MYO-D), and tandem repetitive ribosomal DNA (rDNA) showed a 20-25 fold enrichment in MPB-NP95 SRA samples, and is comparable to the enrichment values in the bt-MBD samples (FIG. 8). Additional work is needed to characterize the DNA fragments that remain bound to the beads by direct linker addition and DNA sequencing.

TABLE 1

High Salt 0.5 M (enriched) peak, no CpG

1
```
1-33      .5  TGTGGGGTTGTTGTTTTGAGAGGGTTTTTTTTGGG
               GTTTTTATTAATGATG
               (SEQ ID NO: 79)
6-33      .5  AAACATTGGGAATATAGTATTTATTTTTGGTGATTA
               TGTGTTTAGTTAAGTATTAGAGGATATTTTTA
               (SEQ ID NO: 28)
7-33      .5  AATTTTTGTAGTTTTAGTAGAGATGGAGTTTTATTA
               TGTTGGTTAGGTTGG
               (SEQ ID NO: 29)
8-33      .5  GAAACAGGAGAATTTTTTGAATTTGGGTGGTAGAGG
               (SEQ ID NO: 30)
9-33      .5  AGAAAATATGGTTTGTTAATGAATGATAGGTTAATT
               TTAGTATGTTGGTTATTTTAATATTTTGTTATTAGT
               TGGTTTGG
               (SEQ ID NO: 31)
H19-33    .5  CAGGTATAGTGGTAAGAATTTGTAGTTTTAGTTATT
               TGGGAGGTTGAGTTAGGA
               (SEQ ID NO :32)
H76-33    .5  AAACTTTTGGTTGGGGGTGGTGGTTTATGTTTGTAA
               TTTTAGTATTTTGGGAGGTCAAGGTGAGTGGAT
               (SEQ ID NO: 33)
H2-33     .5  AGGTAGTTTTATTTTGGGTTTTAGGGAATAGGAGGG
               AATTAGAAGGA
               (SEQ ID NO: 34)
H5-33     .5  CAGTATTTTGGGAGGTTAAGGTAGGTGGATTATGAG
               GTTAGGAGATTGAGA
               (SEQ ID NO: 35)
H21-33    .5  GATGGATTGTTTGAGTTTAGGAGTTTGAGATTAG
               (SEQ ID NO: 36)
H24-33    .5  5TGAGTTTAGTTTAAGTTGATTGGGTAGGTAAATGT
               TTGTTATGAATTTGGAAGTGAGAGA
               (SEQ ID NO: 37)
```

High Salt 0.5 M (enriched) peak, CPG

```
3-33      .5  725439 bp at 3' side: nuclear
               receptor subfamily 4, group A,
               member 2 isoform a
               CAGGTGTTGAGTGGTGAGGGATGTGTAAATAAGTAA
               GTGTGGGGTTCGGTTATTGCGTATAGTTAGGTATAT
               TGGTTGTTGTGGGGTGGGGTAGGTAATTTAAGTATT
               AGTATGGGTATTGGTTTTTTGTGAGGC
               (SEQ ID NO: 38)
```

TABLE 1-continued

```
4-33      .5  Fanconi anemia, complementation
               group M
               ACAAAAATTAGTTAGGTATAGTGGTATGTATTTGTA
               GTTTTAGTTAATCGGGATCCTGA
               (SEQ ID NO: 39)
5-33      .5  GENE ID: 10692 RRH|retinal pigment
               epithelium-derived rhodopsin homolog
               GAATGGCAAGTATTGGATTATTTACGGTCGTGGTTG
               TGGATCGATA
               (SEQ ID NO :40)
10-33     .5  transglutaminase 2 isoform b
               AGTTTGTACGGTGAAGTTTAGGTTTTATTGTGGATA
               CGGTTGAAATAGAAGAGTGATGGG
               (SEQ ID NO: 41)
H6-33     .5  31781 bp at 5' side: von Willebrand
               factor preproprotein 46059 bp at 3'
               side: CD9 antigen
               TGAACGCGGGAGGCGGAGTTTGTAGTGAGTTAAGAT
               CGCGTTATTGTATTTTAG
               (SEQ ID NO :42)
H7-33     .5  ref|NW_001838799.1|Hs2_WGA192_36
               GGAAACGAATGAAATTATCGAATGGAATCGAATGGT
               GTTATCGAACGGA
               (SEQ ID NO :43)
H12-33    .5  coagulation factor XIII A1 subunit
               precursor
               CGGATAGGAGGGGTTGTTATGAAG
               (SEQ ID NO: 44)
H15-33    .5  545337 bp at 5' side: EGF-like
               repeats and discoidin I-like
               domains-containing
               TAGTTAATTATATGTGTTCGTTATTTGTGTATGTGG
               (SEQ ID NO: 45)
H45-33    .5  114563 bp at 5' side: similar to
               hCG2036843
               ATGAAAGTGTTTTGGGGATGGATGGGGGATATGGTT
               GTATAATGTGGCGGACG
               (SEQ ID NO :46)
H55-33    .5  B-cell novel protein 1 isoform a
               AGAATCGTTTGAGTTTAGGAGTTTAAGATTAGTTTG
               GGTAATATAGTGAGATTTTGTTGTTACGAAAATAAA
               TAAAAAATTAGTTAGGTGTGGTGGTGTATGTTTGTG
               GT
               (SEQ ID NO: 47)
H64-33    .5  17408 bp at 5' side: musashi 2 iso-
               form b
               TGTTTGTTGAGTGTACGTNTNNNGTATTTGTGTTGG
               GTGTATGTGGATGTGTGNGNTGAG
               (SEQ ID NO: 48)
H74-33    .5  Homo sapiens HECT domain containing
               1 (HECTD1), mRNA
               AGTTTGAAGTTTTTATAGAAGAAGGTTATGATTTAT
               TTTCGGTAGGAAGTTTTGAAGAG
               (SEQ ID NO: 49)
H15a-33   .5  62438 bp at 5' side: D-amino acid
               oxidase activator
               AGGAAAGTTGGAAGGATGAGGATAACGTAGTGTTTT
               GTTGAAGAAGGAAGAGANNNNGGATTAAATTGAAAT
               TGATTGGGTTTYTAAAATGGATGGGAT
               (SEQ ID NO: 50)
H27-33    .5  unc-51-like kinase 4
               AGTTTGATTTTAGATTGTTGTGTTAGTAATGAGCGA
               GG
               (SEQ ID NO: 51)
H30-33    .5  spectrin repeat containing, nuclear
               envelope 2 isoform 1
               TTATTTTTATAAAAATAAAAAAATTAGTTGGGTGTA
               GTGGCGTATGTTTGTNGTTTTAGT
               (SEQ ID NO: 52)
H H31-33   .5  256834 bp at 5' side: alpha 1 type
               IV collagen preproprotein
               AACGATAAAGAAAATAAAAGGAGTGAGGGAGGATAG
               ATGGG
               (SEQ ID NO: 53)
H35-33    .5  pumilio 1 isoform 1
               ATTAGTTAGGCGTGGGGGTGGGTGTTTGTAGTTTTA
               GTTATTTAGGAGGTTGAGGTAGGA
               (SEQ ID NO: 54)
```

TABLE 1-continued

| | | |
|---|---|---|
| H7a-33 | .5 | zinc finger and BTB domain containing 46<br>AAGGTGGGGGTTGGGGGGNTNGTTTTTTCGGGNTGT<br>TGTCGCGGNGGAGGAGCGTTTTAGAGTTTTACGGCGT<br>AGTTTTATTCGTCGGNATTTAGGTGGACGTTGATCG<br>GGGGAGAGAATTGAGTATCGGGATC<br>(SEQ ID NO: 55) |
| H9-33 | .5 | 259088 BP AT 3' SIDE: CHROMODOMAIN PROTEIN, Y-LIKE 2<br>AGAGTAGAGAGATGATTAAATTTATGTTAATTTTAT<br>TATTTTGGTTTTGAGGTTGTTGTRYAAGTTTTTTAG<br>AATGTGAGTCGGGTATTGTTTTGAGGTTAACGTTA<br>TTTGGTTTGCGTTT<br>(SEQ ID NO: 56) |

Low Salt 0.3 M (control) peak, CPG

| | | |
|---|---|---|
| 13-33 | .3 | GGGAGGTAGTGATGAGAGTAATAGATAGGGTTTAGG<br>TGTTTGTGTATGATATGTTTG<br>(SEQ ID NO: 57) |
| L9-33 | .3 | GATGTTATTAAATAATTAGATTATTTGTATTCGAAT<br>TGGGTAAGTAGTATAAAGGANAANGATATTATTAAA<br>TAATTAGACTATTTGTATTCGAATTGGGTAAGTAGT<br>ACAAAGGAGAAGTGGGGNAA<br>(SEQ ID NO: 58) |
| 3-2-33 | .3 | 19744 bp at 3' side: Myc-binding protein-associated protein<br>TTTGTAGAAGGATGTGAGAGGAGAAGTGAGCGGTTT<br>TATAGGTATGATGTTAGTTATAAGGGGTTGGTGAGT<br>TGATGTGGGAGGATTATTTGGTTTAGGAGTTTAAGG<br>TTGCGGTGAGT<br>(SEQ ID NO: 59) |
| L-17.33 | | dihydrouridine synthase 3-like<br>TGAGGGTTGGGTTTAGGATAGAGTATAGAGAGGGAG<br>ATTTAGTTAGGAGTTTTTTAAGGTATATAGTTTTT<br>GATTTTTAGGTAGTTAGAATAGGAACGTGGATATAG<br>TTGGTATTTAATAGACGTATATTAGATGGATAGATT<br>TGTTATTGA<br>(SEQ ID NO: 60) |

Low Salt 0.3 M (control) peak, no CpG

| | | |
|---|---|---|
| 3-5-33 | .3 | TAGTAGTATGATGTTAGTTTTTTTAAATTATAGAT<br>TCAATAANATTCAGTTAAAATTTTATTAGTTTTATT<br>TATTTATTGATTTAGTAGAGATGGATATAGTACTGT<br>(SEQ ID NO: 61) |
| 3-6-33 | .3 | GTGTTATCGTATTGGGGTTATTTGTGTAATTAATAT<br>GTGTTATTTAGTTTTAGGGTGTATGTTTATTGTTTT<br>AATTATGATGGAGGTGTAGTTTGGAGATTTTGTGTT<br>AGGAGATAGAGTTTGGGGTTTTAAGGGGATTT<br>TTTGTGGGGGAGAGGGATAGTTGTGTAGTAGAGTGA<br>TAATGAAGGTTTTTGATTTAATGTGTAGTTTTTAGG<br>TTATGTGT<br>(SEQ ID NO: 62) |
| 3-8-33 | .3 | TTTGGGAGGTTGAGGTGGGTAGATTATGATGTTAAG<br>AGATTGAGATTAT<br>(SEQ ID NO: 63) |
| L1-33 | .3 | GATGAAAGGTTAAAATTGAGATAGAAGATGTGATTT<br>GGAAGGTTATAAGAGAAGTTGGATAAAGTTAAATAA<br>GGA<br>AAGGAATTTAGAAAAAAGTGTTTAATGTTGTAGAAG<br>G<br>(SEQ ID NO: 64) |
| L1-19 | .3 | CTATTCTTCCCATTCTCAACATAACTCTAACCTTCC<br>TTCATCCTCACACCCAACAATCATTCACTCATTTAT<br>CTA<br>(SEQ ID NO: 65) |
| L-1.33 | | GATAAAGTTGTGNGTAGGGATTTTTGGTAGAGGGAA<br>TAGAAAGATGGAGGTGTTGAGGTAGGAGTGATGGGT<br>AGGTTTGAAGAGTAGAGTTTAGTGTAGTGAGGGGGT<br>TATTAGTAAGGG<br>(SEQ ID NO 66) |
| L-11.33 | | ATATTTTATGGAGGAGTAATTTTTAGAGTATATGGA<br>TTGGTTTTATGGAGGAAGATTGTTATTTATAGGTTG<br>GTGTAAGTGATGGTAGTAGTGGTTTGTC<br>(SEQ ID NO: 67) |
| L-12.33 | | AGAAGATAAGGAGAAGATAATTATTNTTTTGGTAGA<br>GGTAATTGATTTGATTATTAGGA<br>(SEQ ID NO: 68) |

TABLE 1-continued

| | |
|---|---|
| L-15.33 | ATGTGTATTTAAAGTAAGGTTATGAGATTTTGGATT<br>GTTTTTTGTTTAGGATGATATGTG<br>(SEQ ID NO: 69) |
| L-16.33 | AAGTAAAATAATTTTGTTTTTATTTATTTTANAGGA<br>TTGTT<br>(SEQ ID NO: 70) |
| L-18.33 | AAAATTTTAAGATTAGGTAAAAATATTGTGTAAAGT<br>GAGAGGGATGTGATGGTTAAAAAGTGATTTAAGATT<br>TTTGTAATTTTTAGTTATAATTTAAGA<br>(SEQ ID NO: 71) |
| L-2.33 | GAGATAATAGTGAGTATGATATTTTTGTTTTTTT<br>ATTATGTGTTAAGTATTGTTTAGGGATTAAGTGGGG<br>TTGTGTTTATTGTAGATGTTGTAGGTATGGAGTTAG<br>TA<br>(SEQ ID NO: 72) |
| L-20.33 | ATGTATTTAGTTGTTTATTGAATATTATTTTAATAT<br>TGTATTATGAATATTGTTATGTTATGGATTTTAGGT<br>TTTATTAGATTGGTATTAGTATCATTTAGGAATATT<br>TTATGATGTGTGTTGATAAATTTTTAAGATAAATGA<br>ATTTGAGATATGTGTGAGTATTTTATAAAATAAATT<br>TTGTTGGA<br>(SEQ ID NO :73) |
| L-23.33 | ATGGTTTGTTTGTTTTTGTGGAAAATGGTATGAAGA<br>TTGGGTTTGTATTGAATTTG<br>(SEQ ID NO :74) |
| L-24.33 | TGTAGTTTTAGTTATTTAGGAGGTTGAGATATGAGA<br>ATTATTTGAATTTGGGGGGGGAAGGTTGTAGTGA<br>(SEQ ID NO: 75) |
| L-27.33 | TGAGAAGGGGGTAGTGGGGATGGTTTTGTGGGTTTA<br>TGTTGTTTTTGATTTTAGAAAATAAAGTTTTTTGTA<br>GGAAGTAGGTGGGAAGTAAATTTGTTGATAAGTGTAA<br>AGATTTGGGAATTATATTAAGGGGTAAATGGAGGAN<br>AGGTGTTGGTGTTAANGAGGTAGACNTATGGGAGTT<br>NGGTTTTAGGAANGGNNGTGGNTAGAAAGG<br>((SEQ ID NO: 76) |
| L-28.33 | GGTAGGTAGATTATTTGAGGTTAGGAGTTTAAG<br>(SEQ ID NO: 77) |
| L-4.33 | ATATTTTTTATTGAAGAATGTAGTTTTTTAAAATT<br>AAAATGTATTTTTAAAATTTATTTATTATTTTTT--<br>GAGATAAGGTTTTGTTTTGTTGTTTAAGTTAGAGTA<br>TAGTATGTGATTATAGTTTATTGTAGTTTTGAATTT<br>TTGGGTTTAAG<br>(SEQ ID NO: 78) |

Table 1 above shows the results of sequence analysis of the two NaCl peaks from the SRA-domain column showed a better than 10-fold enrichment of methylated CpG DNA. Out of 30 reads with an average size of 63 bases in the high (0.5 M) NaCl fraction, 19 contained at least one methylated CpG. Of the 1900 bases sequenced, 44 were methylated CpG or 2.32% of the total. Out of 22 reads with an average size of 105 bases in the low salt 0.3M peak, 3 contained methylated CpG. Of these 2327 bisulfate-converted bases, 5 were identified as methylated CpG or 0.215% of the total.

REFERENCES

1. Bird, A P (1986) Cpg-rich islands and the function of DNA methylation. Nature 321: 209-213.
2. Bird, A P (2002) DNA methylation patterns and epigenetic memory. Genes Dev 16: 6-21.
3. Shen L, Kondo Y, Guo Y, Zhang 3, Zhang L, et al. (2007) Genome-wide profiling of DNA methylation reveals a class of normally methylated CpG island promoters. PloS Genet. 3(10): e181.
4. Illingworth R, Kerr A, DeSousa D, Jørgensen H, Ellis P, et al. (2008) A novel CpG island set identifies tissue-specific methylation at developmental gene loci. PloS Biol 6(1): e22.
5. Reik W (2007) Stability and flexibility of epigenetic gene regulation in mammalian development. Nature 447: 425-432.
6. Heard E, Clerc P, Avner P (1997) X-Chromosome inactivation in mammals. Annu Rev Gent 31: 571-610.

7. Sado T, Fenner M H, Tan S S, Tam P, Shioda T, et al. (2000) X inactivation in the mouse embryo deficient for Dnmt1: distinct effect of hypomethylation on imprinted and random X inactivation. Dev Biol 225: 294-303.
8. Ueki T, Walter K, Skinner H, Jaffee E, et al. (2002) Aberrant CpG island methylation in cancer cell lines arises in the primary cancers from which they were derived. Oncogene 21(13): 2114-2117.
9. Das R, Dimitrova N, Xuan Z, Rollins R, et al. (2006) Computational prediction of methylation status in human genomic sequences. PNAS 103 (28): 10713-10716.
10. Hendrich B, Bird A (1998) Identification and Characterization of a Family of Mammalian Methyl-CpG Binding Proteins. Mol Cell Biol. 18(11): 6538-6547.
11. Frommer M, McDonald L E, Millar D S, Collis C M, Watt F, Grigg G W, Molloy P L, Paul C L (1992) A genomic sequencing protocol that yields a positive display of 5-methylcytosine residues in individual DNA strands. Proc Natl Acad Sci USA 89:1827-183.
12. Xiong Z, Laird P, (1997) COBRA: a sensitive and quantitative DNA methylation assay. Nucleic Acids Research 25(12): 2532-2534.
13. Herman J G, Graff J R, Myohanen S, Nelkin B D, Baylin S B: Methylation-specific PCR: a novel PCR assay for methylation status of CpG islands. Proc Natl Acad Sci USA 1996, 93:9821-9826.
14. Cokus S, Feng S, Zhang X, Chen Z, Merriman B, Haudenschild C, Pradhan S, Nelson S, Pellegrini M, Jacobsen S (2008) Shotgun bisulphite sequencing of the *Arabidopsis* genome reveals DNA methylation patterning. Nature 452, 215-219.
15. Bostick M, Kim J K, Estève P O, Clark A, Pradhan S, Jacobsen S (2007) UHRF1 Plays a Role in Maintaining DNA Methylation in Mammalian Cells Science 21(317): 1760-1764.
16. Deininger P L, Batzer M A. (2002) Mammalian retroelements. Genome Research. 12(10): 1455-1465.
17. Reinders J, Céline Delucinge Vivier C D, Theiler G, Chollet D, Descombes P, Paszkowski J (2008) Genome-wide, high-resolution DNA methylation profiling using bisulfite-mediated cytosine conversion. Genome Res. 18(3): 469-476.
18. Song L, James S R, Kazim L, Karpf A (2005) Specific Method for the Determination of Genomic DNA Methylation by Liquid Chromatography-Electrospray Ionization Tandem Mass Spectrometry. Anal. Chem., 77 (2): 504-510.
19. Borczuk A C, Kim H K, Yegen H A, et al. (2005) Lung Adenocarcinoma Global Profiling Identifies Type II Transforming Growth Factor-13 Receptor as a Repressor of Invasiveness. American Journal of Respiratory and Critical Care MedicinE, 172: 729-737.
20. Jacquemont C, Taniguchi T, The Fanconi anemia pathway and ubiquitin (2007) BMC Biochem., 8(Suppl 1): S10.
21. British Journal of Haematology, (2004) 126 (6): 893-896
22. Lu S, Davies P, Regulation of the expression of the tissue transglutaminase gene by•DNA•methylation. (1997) PNAS, 94(9): 4692-4697.
23. Rousseaux S, Caron C, Govin J, Lestrat C, Faure A K, Khochbin S, (2005) Establishment of male-specific epigenetic information. Gene, 345 (2): 139-153.
24. Boumber Y A, Kondo Y, Chen X, Shen L, Gharibyan V, et al., Kazuo, (2007) RIL, a LIM Gene on 5q31, Is Silenced by Methylation in Cancer and Sensitizes Cancer Cells to Apoptosis. Cancer Research 67: 1997-2005.
25. Carrasco D, Tonon G, Huang Y, Zhang Y, Sinha R, Feng B, Stewart J, Zhan F, Khatry D, Protopopova, M. (2003) High-resolution genomic profiles define distinct clinico-pathogenetic subgroups of multiple myeloma patients. Cancer Cell, 9(4): 313-325.
26. Filion G J P, Zhenilo S, Salozhin S, Yamada D, Prokhortchouk E, Pierre-Defossez P A. (2006) A Family of Human Zinc Finger Proteins That Bind Methylated DNA and Repress Transcription Mol Cell Biol. 26(1): 169-181.
27. Li Z X, Ma X, Wang Z H. (2006) A differentially methylated region of the DAZ1 gene in spermatic and somatic cells. Asian Journal of Andrology. 8(1): 61-67.

What is claimed is:

1. A method for enriching for single stranded CpG methylated polynucleotides from a mixture containing methylated and unmethylated polynucleotides, comprising:

allowing the single stranded polynucleotides in the mixture to bind to a polypeptide having at least 90% amino acid sequence homology with SEQ ID NO:3;

eluting the unmethylated single stranded polynucleotides from the polypeptide in a solution containing a low concentration of a salt; and eluting the methylated single stranded polynucleotides from the polypeptide in a solution containing a high concentration of a salt.

2. A method according to claim 1, wherein a low concentration of the salt is less than 0.4 M salt.

3. A method according to claim 1, wherein a high concentration of the salt is 0.4 M-0.6 M salt.

4. A method according to claim 2 or claim 3, wherein the salt is NaCl.

* * * * *